United States Patent [19]

Krivi

[11] Patent Number: 5,141,922

[45] Date of Patent: * Aug. 25, 1992

[54] BIOLOGICALLY ACTIVE PROTEINS AND A METHOD FOR THEIR USE

[75] Inventor: Gwen G. Krivi, Olivette, Mo.

[73] Assignee: Monsanto Company, St. Louis, Mo.

[ * ] Notice: The portion of the term of this patent subsequent to Aug. 6, 2008 has been disclaimed.

[21] Appl. No.: 729,283

[22] Filed: Jul. 12, 1991

Related U.S. Application Data

[63] Continuation of Ser. No. 824,202, Feb. 4, 1986, Pat. No. 5,037,806, which is a continuation-in-part of Ser. No. 704,362, Feb. 22, 1985, Pat. No. 4,861,868.

[51] Int. Cl.$^5$ ............................................. A61K 37/36
[52] U.S. Cl. ........................................ 514/12; 514/21; 530/324; 530/399
[58] Field of Search ............... 514/2, 12, 21; 530/324, 530/399

[56] References Cited

U.S. PATENT DOCUMENTS

| | | | |
|---|---|---|---|
| 4,693,973 | 9/1987 | Buell | 435/68 |
| 4,861,868 | 8/1989 | Krivi | 530/399 |
| 5,037,806 | 2/1986 | Krivi | 514/12 |

OTHER PUBLICATIONS

Wallis, FEBS Letters, 3(2), 118–120 (Apr. 1969) Seavey et al. Biochemical & Biophysical Research Communications, 43(1), pp. 180–195 (1971).
Fernandez et al., FEBS Letters, 18(1), 53–54 (1971).
Wallis, FEBS Letters, 35(1), 11–14 (1973).
Santome et al., Eur. J. Biochem., 37,164–170 (1973).
Graf et al., Biochemical & Biophysical Research Communications, 56(1) 168–175 (1974).
Hart et al., Biochem, J., 218, 573–581 (1984).
George et al., DNA 4(4), 273–281 (1985).
Ellis et al., Growth Hormone, Exerpta Medica, Amsterdam, Int. Congr. Ser. No. 244, 55–67 (1972).

Primary Examiner—F. T. Moezie
Attorney, Agent, or Firm—Wayne R. Eberhardt; George R. Beck

[57] ABSTRACT

A method for preparing polypeptides in bacteria with an alanine rather than a methionine at the N-terminus. The DNA sequence expressed has an alanine codon immediately following from at least one methionine codon, and allows for the expression of polypeptides having the amino acid sequence essentially the same as such naturally occurring eucaryotic protein as various bovine and porcine somatotropin species. In another important embodiment, the invention provides a class of compositions comprising certain valine-containing somatropin species which increase milk production in lactating mammals to a significantly greater extent than otherwise-identical leucine somatotropin species.

13 Claims, 10 Drawing Sheets

FIGURE 9
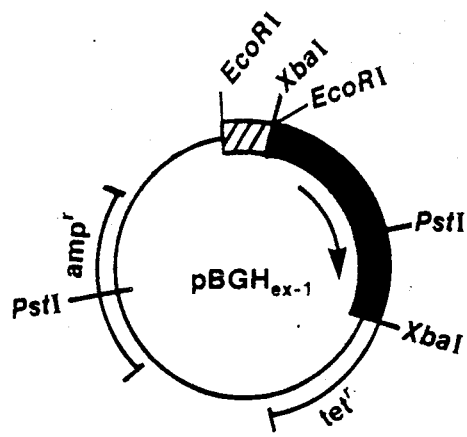
1. Partial EcoRI Digest
2. S1 Nuclease To Remove Sticky Ends
3. T4 DNA Ligase
4. Transform E.coli, Select amp$^r$, tet$^r$ Colonies
5. Screen For 590 bp EcoRI/HindIII Fragment And 1050 bp EcoRI/PstI Fragment
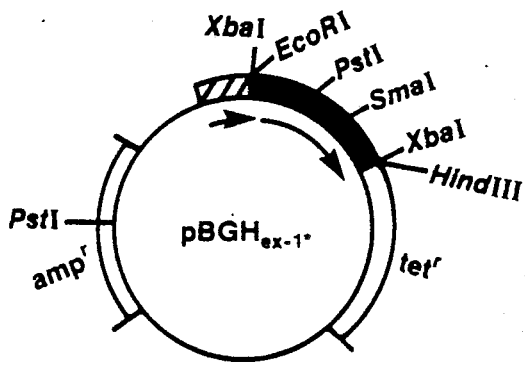

BIOLOGICALLY ACTIVE PROTEINS AND A METHOD FOR THEIR USE

CROSS REFERENCE TO RELATED APPLICATIONS

This application is a continuation of Ser. No. 824,202 filed Feb. 4, 1986, now U.S. Pat. No. 5,037,806, which was a continuation-in-part of Ser. No. 704,362 filed Feb. 22, 1985, now U.S. Pat. No. 4,861,868.

TECHNICAL FIELD

The present invention is directed to a method of expressing heterologous DNA sequences (e.g. eucaryotic genes) in procaryotic organisms. In one important embodiment, the invention is directed to production in procaryotes of polypeptides having an N-terminal alanine and to various N-alanyl polypeptides that can be produced by that method. Also included is a class of valine bGH (bovine growth hormone) species that enhance milk production to an unexpectedly great extent.

BACKGROUND OF THE INVENTION

Expression of genes by eucaryotes and procaryotes, while sharing the same basic steps of gene transcription into messenger RNA (mRNA) and subsequent translation of that mRNA into proteins, employ different sets of intracellular controls for these steps.

Additionally, in eucaryotes many mature proteins are first translated as pre-proteins; i.e, polypeptides comprised of the mature protein's sequence fused to a leader or signal sequence. Eucaryotic mRNA encodes the entire pre-protein, which is processed after translation to remove the leader sequence and provide the mature protein. While eucaryotic cells are equipped to specifically process such pre-proteins into mature proteins, procaryotic cells are generally not able to recognize the processing signals present in eucaryotic proteins. Thus, if complete complementary DNA (cDNA) transcripts of eucaryotic mRNA are employed as the DNA sequences for expression in procaryotes, the pre-protein, not the mature protein, is found. It is possible to convert pre-proteins to mature proteins in vitro, but not without significant expense.

In the event that the DNA sequence encoding the mature protein is used for mature protein expression in procaryotes, this sequence will be lacking the eucaryotic translation and post-translation processing signals usually contained within the DNA for the leader sequence. Therefore, for expression of cloned eucaryotic genes or other heterologous DNA sequences in procaryotic systems, it has proven desirable to employ procaryotic control signals for reasons of efficiency and because eucaryotic signals may not be recognized by a procaryotic host cell.

The term "heterologous DNA" is defined herein as DNA at least a portion of which is not normally contained within the genome of the host cell. Examples of heterologous DNA include, but are not limited to, viral and eucaryotic genes, gene fragments, alleles and synthetic DNA sequences. The term "heterologous protein" or "heterologous polypeptide" is defined herein as a protein or polypeptide at least a portion of which is not normally encoded within the genome of the host cell.

The procaryotic control signals include a promoter which signals the initiation of transcription and translation control signals comprising a ribosome binding site, a translation start signal and a translation stop signal. All of these signals except the translation stop signal must be situated in front of the eucaryotic gene or other DNA to be expressed.

The art has adopted several approaches to expressing heterologous DNA (e.g. eucaryotic genes) in procaryotes. In one approach, the DNA segment encoding the resultant protein is ligated to the DNA encoding all or part of a bacterial protein under the control of its bacterial promoter. The endogenous procaryotic DNA necessarily also contains the ribosome binding site and translation start signal. Expression of such ligated DNA results in what is called a fusion protein comprising the eucaryotic polypeptide linked or fused to a whole or partial bacterial protein. Isolation of the eucaryotic protein may then be achieved by site-specific enzymatic or chemical cleavage at the endogenous-eucaryotic protein fusion site or by selective degradation of the procaryotic polypeptide sequences.

Examples of published works relating to the production in bacteria of eucaryotic fusion proteins include European Application 47,600 (published Mar. 17, 1982) which refers to fusion and non-fusion proteins comprising bovine pre-growth hormone or bovine growth hormone ("bGH") at the carboxy(C—) terminus with or without a portion of a procaryotic protein at the amino (N-) terminus; U.K. Patent Application GB 2,073,245A (published Oct. 14, 1981) referring to fusion proteins of bGH and $E.$ $coli$ $\beta$-lactamase; E. Keshet et al., *Nucleic Acid Research*, 9:19-30 (1981) referring to a fusion protein of bGH and $E.$ $coli$ $\beta$-lactamase; European Patent Application 95,361 (published Nov. 30, 1983) referring to a fusion protein comprising, in sequence, an endogenous protein at the N-terminus, a translation start signal amino acid, an enterokinase cleavage site, and an exogenous protein (e.g. growth hormone) at the C-terminus. This fusion protein approach, however, is cumbersome in that it requires in vitro processing following purification, and the cost cf enzyme(s) for processing commercial quantities can be prohibitive.

Fusion proteins, however, have become an attractive system for expressing some eucaryotic genes or other heterologous DNA in procaryotic cells, as the fusion product appears to protect some of the resulting heterologous proteins from intracellular degradation. Bacterial cells appear to recognize some eucaryotic proteins produced therein as foreign and, thus, proceed to degrade these proteins as soon as the proteins are made or shortly thereafter. Fusion proteins engineered for protective purposes can employ endogenous polypeptide sequences at either the amino or carboxy terminus of the heterologous protein. An example of the latter approach is found in European Patent Application 111,814 (published Jun. 27, 1984) describing fusion proteins comprising a form of bGH having a synthetic front-end (amino-terminus) and $E.$ $coli$ $\beta$-galactosidase at the C-terminus. The advantages are, again, diminished by the need to subsequently cleave the heterologous protein from the endogenous polypeptide as discussed above.

In another approach, the translation start signal, ATG, under the control of a bacterial promoter, is located immediately preceding the DNA sequence encoding a heterologous (e.g. eucaryotic) protein free from endogenous protein at both the N- and C-termini of the protein produced. Although the proteins produced by such gene constructs do not require subsequent cleavage to generate the desired protein, they typically include a methionine (in some cases a formylmethionine) at the N-terminus as the ATG start signal is also a methionine codon. Thus, unless the desired mature protein begins with methionine, the protein will now have an N-terminus altered by inclusion of that methionine residue.

Examples of such gene constructs include Guarente et al., *Cell* (1980) 20:543–553 wherein the rabbit β-globin gene, which possesses an N-terminal valine, is expressed in *E. coli* employing the gene construct just described. The investigators found that whereas "In rabbit β-globin, there is no amino terminal methionine, and leucines are found at positions 3, 14, 28, 31, 32 ... .In the labeled protein, leucines were found at positions 4, 15, 29, 32 and 33, and a methionine was found at position 1. This result shows that the protein is rabbit β-globin plus an amino terminal methionine which is not removed in *E. coli.*" Id at 546–547.

Another example relates to the production of growth hormones in bacteria employing the above-described gene construct. Schoner et al. *Proc. Nat'l. Acad. Sci. U.S.A.* (1984) 81:5403–5407 describes a high level expression system in bacteria for production of bGH which results in production of an N-methionyl bGH; that is, a compound having an amino acid sequence like that of one of the naturally-occurring bGH species plus a methionine at its N-terminus. The addition of an N-terminal methionine to various growth hormone species produced in bacteria is again discussed in European Patent Application 103,395 (published Mar. 21, 1984) and European Patent Application 75,444 (published Mar. 30, 1983), for bGH, and Seeburg et al., *DNA* (1983) 2:37–45, for bGH and porcine growth hormone ("pGH").

Addition of an N-terminal methionine to the natural N-terminus may be undesirable for several reasons. First, it is possible (although currently believed unlikely) that the methionine may tend to make the protein antigenic in an organism in which the protein without the N-methionine is endogenous. Second, the addition of methionine to the N-terminal portion of the protein may have an undesirable effect on its bioactivity or its physical properties. Third, this altered form of the protein may hinder scientific efforts in determining the relationship of the natural protein's function to its structure. Further, it may be advantageous to have a biosynthetic protein which is structurally as close as possible to a naturally-occurring protein when applying for governmental approval of medical or veterinary applications.

The ability of such procaryotes as bacteria to remove the N-terminal methionine from proteins either during their production or thereafter has been a topic of considerable interest. For example, Waller, *J. Mol. Biol.* (1963) 7:483–496, examined the N-terminal amino acid composition of "soluble" and ribosomal proteins from a cell-free extract of *E. coli*, and European Patent Application 103,395 (published Mar. 21, 1984) discloses the removal of an N-terminal methionine from an eucaryotic protein produced in *E. coli*. Specifically, methionine is removed from one of two bacterially-produced bGH proteins both of which contain a serine residue immediately following to the originally-present N-terminal methionine. The gene construct employed in these studies, however, comprised a synthetic start sequence coding for 5'-methionine-serine-leucine-3' inserted immediately adjacent to the 5' end of a bGH coding sequence in which bases coding for the first 4 or 9 naturally-occurring amino acids had been deleted. Thus, the resultant protein produced in *E. coli* was a nonnaturally-occurring protein. U.K. Patent Application 2,073,245A (published Oct. 14, 1981) discloses that when met pro replaces ala in the mature bGH protein, "Met can be processed by bacteria to give modified bGH starting with the amino acid sequence Pro Phe Ala Pro".

There is, thus, a need to develop an economic and predictable means for producing in such microorganisms as bacteria heterologous (e.g. eucaryotic) proteins that do not have an N-terminal methionine. Specifically, it is especially desirable to develop a method whereby such proteins produced in bacteria do not require in vitro, post-fermentation processing and do not contain an additional, non-naturally occurring N-terminal methionine.

Growth hormones (also called somatotropins) are polypeptides produced and secreted by cells of the pituitary gland and are largely species-specific in their actions. In addition to their role in promoting skeletal growth, growth hormones affect a variety of metabolic processes including the stimulation of lactation, increased insulin release from the pancreas and glucagon secretion, and they exert a lipid-mobilizing effect. Exogenous administration of bGH to cattle, for example, has been demonstrated to increase milk production, feed efficiency and/or growth rate, decrease fattening time and increase the lean-to-fat ratio. It is still not fully understood, however, how the hormone exerts these multiple effects.

Extensive work with human growth hormone (hGH) has established that the hormone, as secreted by the human pituitary gland, is not a single molecular entity but a mixture of polypeptides. Fractionation of the various hGH species has resulted in the preparation of some hGH fractions with neither diabetogenic or lipolytic activities.

Similarly, bGH is produced by cattle in multiple forms. Specifically, four forms of bGH are produced which differ at two positions of the protein. The N-terminal amino acid can vary due to a presumed ambiguity in removal of the signal-peptide (leader) sequence so that the mature protein begins with either NH$_2$-phe-pro or NH$_2$-ala-phe-pro. In addition, there is a heterogeneity at amino acid 126 being either a leucine or a valine. This is apparently due to an allelic variation in the bovine population. Wallis (1969) *FEBS Letters* 3 118–120; Fellows and Rogol (1969) *J. Biol. Chem* 244:1567–1575; Fernandez et al. (1971) *FEBS Letters* 18:53–54, Fellows (1973) Personal comments in *Recent Progress in Hormone Research* 29:404: Santome (1973) *Eur. J. Biochem.* 37:164–170; Graf and Li (1974) *Biochem. Biophys. Res. Comm.* 56:168–176. The four molecular forms (species) of pituitary bGH are herein designated and abbreviated as follows:

| Abbr. | Structure |
|---|---|
| bGH(L) | NH$_2$-phe(1)-pro(2) ... leu(126) ... COOH |
| bGH(A,L) | NH$_2$-ala(−1)-phe(1)-pro(2) ... leu(126) ... COOH |
| bGH(V) | NH$_2$-phe(1)-pro(2) ... val(126) ... COOH |
| bGH(A,V) | NH$_2$-ala(−1)-phe(1)-pro(2) ... val(126) ... COOH |

The bGH(A,V) and bGH(V) species are sometimes collectively referred to herein as "valine allelic bGH species" or "valine bGH species". Similarly, the bGH (A,L) and bGH(L) species are sometimes collectively referred to herein as "leucine allelic bGH species" or "leucine bGH species". The numbers assigned to the amino acids in the bGH proteins as abbreviated above are for purposes of identification and reference only.

Mills et al. (1970), *J. Biol. Chem.* 245: 3407–3415, similarly identified two cyanogen bromide fragments of porcine growth hormone (pGH) exhibiting a heterogeneity at their respective N-termini. Specifically, one fragment contained an N-terminal phenylalanine and the other an additional N-terminal alanine. These molecular forms of pGH are herein abbreviated as pGH(P) and pGH(A), respectively.

The entire DNA coding sequences and corresponding amino acid sequences for bGH(L) and pGH(P) have been published by Seeburg et al., *DNA* (1983) 2:37–45, which is incorporated herein by reference.

Pituitary cells of individual cattle have been generally found to contain a mixture of at least bGH(A,L) and bGH(L), or bGH(A,V) and bGH(V). N-terminal analysis of bGH proteins produced in cultured pituitary cells shows an approximately 50:50 mixture of molecules containing either an N-terminal phenylalanine (phe) or an N-terminal alanine (ala). Commercially available preparations, made from pooled pituitaries of many cattle, generally include all four molecular forms of pituitary bGH. Furthermore, it has been reported that about thirty percent of the molecules in bGH preparations obtained from pooled glands have valine replacing leucine at position 126. Ferandez et al. (1971) *FEBS Letters* 18:53–54. Standard biochemical methods for separating the four known bGH forms do not permit production of each or any one of these species on a commercial scale. Differing biological activities of these four forms of bGH would be desirably studied and made commercially available using each of the forms essentially free of one or more of the other three forms, and/or free of other proteins of bovine origin. The term "essentially pure" as used herein to describe a specific protein or proteins means essentially free from proteins and/or other substances with which the protein(s) is (are) associated in a natural environment or source. For those and other purposes, the objects of this invention include a method whereby at least some of those individual forms of bGH can be conveniently produced.

Accordingly, it is an object of the present invention to produce in procaryotes eucaryotic or other heterologous polypeptides which do not have a methionine residue at the N-terminus.

It is another object of the invention to produce in procaryotes eucaryotic or other heterologous polypeptides that do not require in vitro processing to remove a methionine from the N-terminus.

Still another object of the invention is to provide a method for production in procaryotes of eucaryotic or other heterologous polypeptides that have an N-terminal alanine without the need for in vitro processing.

Another object of the invention is to produce in procaryotes eucaryotic or other heterologous polypeptides that have the amino acid sequence essentially the same as a naturally-occurring protein which does not have an N-terminal methionine.

A further object of the invention is to provide a method of producing in procaryotes polypeptides having the amino acid sequence found in mature eucaryotic polypeptides such as bGH(A,L), bGH(A,V) and pGH(A).

It is a still further object of the invention to provide bGH(A,L), bGH(A,V) or pGH(A) substantially free of proteins of bovine or porcine origin, respectively.

It is yet a further object of the present invention to provide a class of bGH species which enhance milk production in cows to an advantageously greater extent.

The bGH polypeptides produced by methods of the present invention provide a means for potentiating such somatotropin activities as increased milk production, growth rate and/or feed efficiency.

These and other objects of the invention will be more fully apparent from the following general and detailed description of the invention.

SUMMARY OF THE INVENTION

Objects of this invention are achieved, in one embodiment, by a method for bacterially producing a heterologous polypeptide having an N-terminal alanine which comprises causing expression of genomic DNA in selected bacteria, said DNA containing from one to about three contiguous methionine codons including a translation start signal, followed immediately by the codons for said polypeptide, followed by a translation stop signal codon, and recovering the resulting heterologous polypeptide having an N-terminal alanine produced within said bacteria.

In another embodiment, the present invention provides a method of producing a heterologous polypeptide having an N-terminal alanine comprising causing expression of genomic DNA in selected bacteria, said DNA containing a translation start signal/methionine codon immediately followed by the codons for said polypeptide, followed by a translation stop signal codon, and recovering the resulting heterologous polypeptide having an N-terminal alanine produced within said bacteria.

In yet another embodiment, the present invention provides a method for preparing in bacteria a heterologous polypeptide containing an amino acid sequence essentially the same as that of a naturally occurring eucaryotic polypeptide.

In other embodiments, the present invention provides various compositions comprising such somatotropins as bGH(A,L), bGH(A,V), pGH(A), and mixtures of bGH(A,L) and bGH(A,V), substantially free of polypeptides of bovine or porcine origin, respectively, or of other somatotropin species.

In still another embodiment, it was discovered that compositions comprising a class of valine bGH species enhance milk production in cows to a greater extent than otherwise-identical leucine bGH species or bGH(A,L). In one preferred embodiment, compositions able to achieve such enhanced milk production, which compositions comprise essentially pure valine bGH species, are provided.

Other embodiments include various genes, DNA vectors and transformed bacteria useful in the aforementioned methods, as well as certain methods utilizing the aforementioned compositions for enhancing bovine and/or porcine lactation, pre-adult growth, and/or feed conversion efficiency.

BRIEF DESCRIPTION OF THE DRAWINGS

In the following diagramatic representations, the hatched box represents the DNA coding sequence for a bacterial promoter, the blackened box represents a heterologous DNA coding sequence, the bars represent additional DNA coding sequences as labeled, and the directional arrow represents the 5' to 3' orientation of the DNA coding sequences. Relevant restriction endonuclease sites are also shown. The DNA regions so marked are for purposes of diagramatic representation only and are not drawn to scale.

FIG. 9 depicts the construction of pBGH$_{ex-1}$* comprising pBGH$_{ex-1}$ wherein the EcoRI restriction endonuclease site located upstream from the 5' end of the ptrp DNA coding sequence has been removed.

DETAILED DESCRIPTION OF THE INVENTION

The present invention provides a method for producing in a procaryote a heterologous polypeptide, such as a eucaryotic (e.g. mammalian or avian) protein, that has an N-terminal alanine. Thus the polypeptide is produced without an N-terminal methionine, and the need for in vitro processing to produce such a polypeptide without an N-terminal methionine is eliminated. The consistent production of such a polypeptide lacking an N-terminal methionine present in the gene coding sequence is a novel and quite unexpected result.

The present invention provides a valuable method for production of essentially pure proteins that have an N-terminal alanine. Such proteins include, without limitation, given species of bovine and porcine somatotropin and variants thereof, the plant proteins ribulose-1,5-bisphosphate carboxylase small subunit, glutathione S-tranferase, and heat shock protein 70. The invention is also useful for the production of other polypeptides where it is desirable to have an alanine at the N-terminus rather than a methionine. It can be desirable to have an N-terminal alanine rather than an N-terminal methionine because, inter alia, the N-alanyl form of the polypeptide may be less immunogenic, or have different physical properties or a modified bioactivity.

In the examples of the present invention wherein essentially pure species of bGH or pGH are produced by bacterial cells, evidence and teachings for removal of the N-terminal methionine are clearly lacking. Indeed, all reports of bGH expression by bacterial cells wherein the N-terminus comprises an N-terminal amino acid sequence homologous to naturally-occurring bGH species report the presence of an N-terminal methionine. In Seeburg et al., DNA (1983) 2:37-45 at 44, the gene sequence for the N-terminal phenylalanine species of bGH, e.g. bGH(L), was deliberately chosen for expression in E. coli, in part to avoid the expected addition of a second hydrophobic amino acid (methionine) to the hydrophobic N-terminal alanine of the other bGH species, i.e., bGH(A,L). Thus, available studies to date teach a retention of the N-terminal methionine in bacterially-produced species of bGH. Notwithstanding these reports, I determined that for the reasons discussed above, there exists a need to produce each of the two bGH species, bGH(A,L) and bGH(A,V), and the pGH species pGH(A). However, attempts to produce these somatotropin species in bacteria were undertaken with the expectation that the polypeptides produced would contain an N-terminal methionine.

Figure 3:
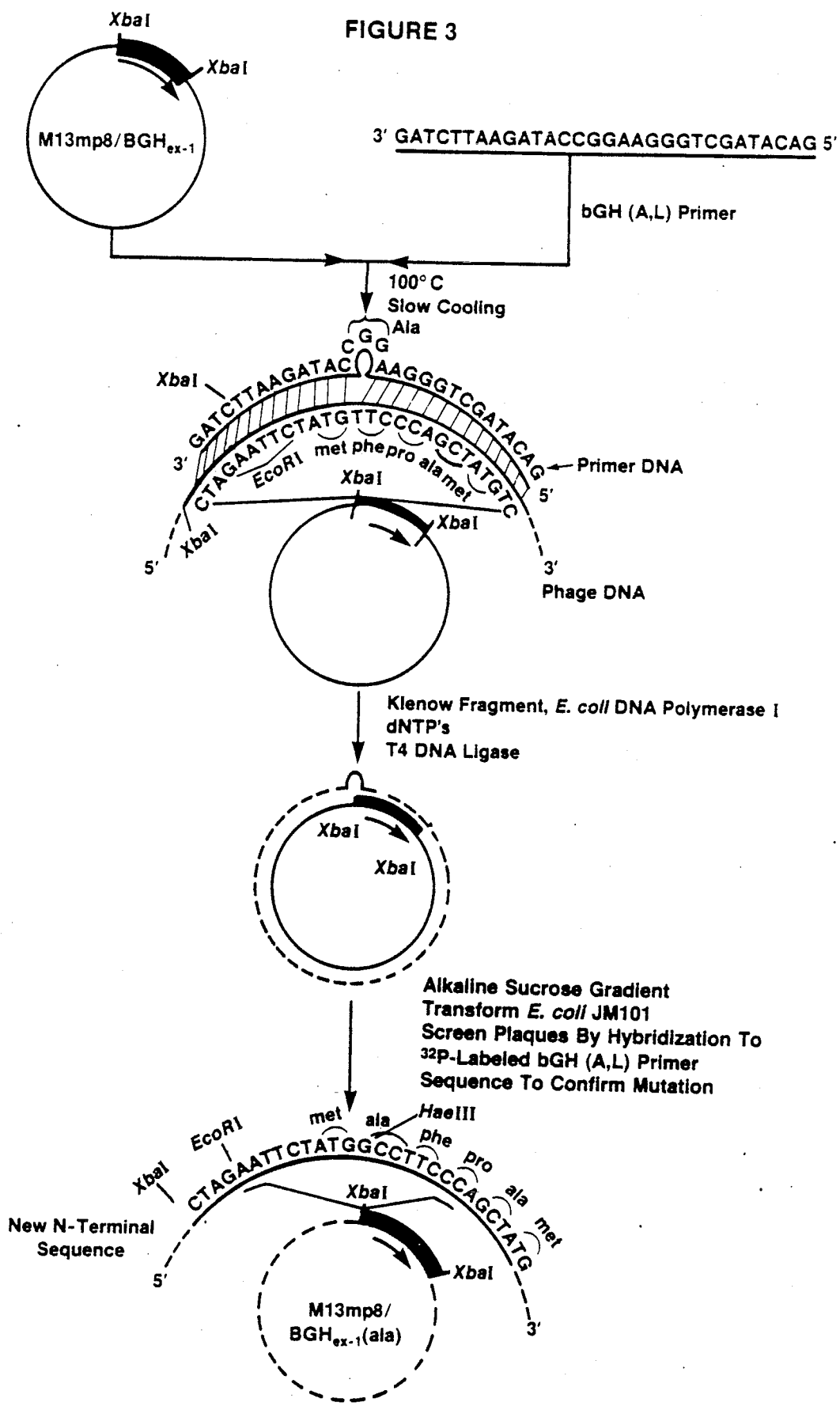
FIG. 3 depicts the creation of a (A,L) DNA coding sequence by oligonucleotide-directed site-specific mutagensis.
Figure 4:
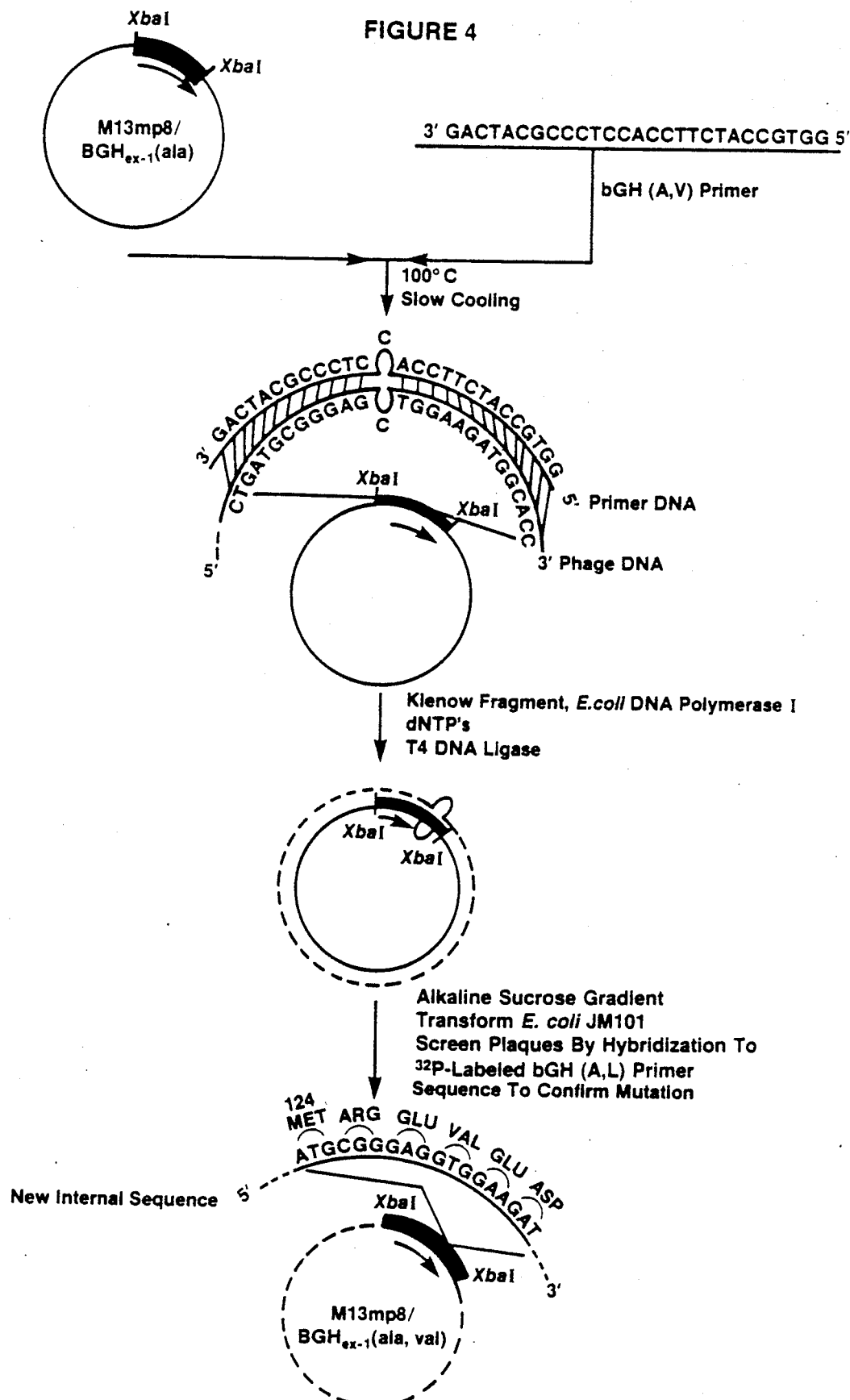
FIG. 4 depicts the creation of a bGH(A,V) DNA coding sequence by oligonucleotide-directed site-specific mutagenesis.
Figure 8:
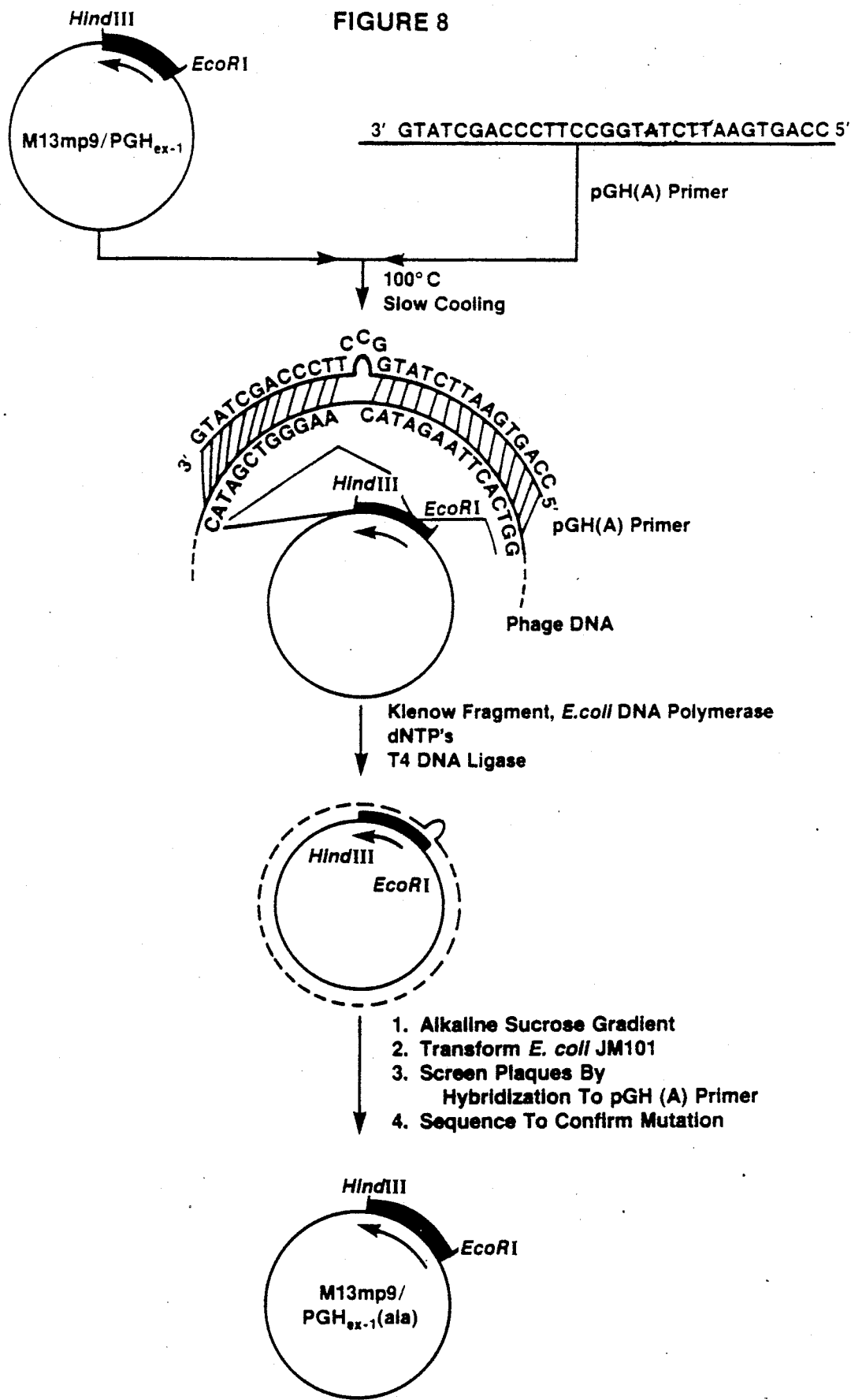
FIG. 8 depicts the creation of a pGH(A) DNA coding sequence by oligonucleotide-directed site-specific mutagenesis.

As detailed in the examples of the present invention, my approach to bGH(A,L), bGH(A,V) and pGH(A) production in bacteria was briefly as follows. The DNA coding sequences for the aforementioned proteins were constructed by oligonucleotide-directed site-specific mutagenesis of the DNA coding sequences for bovine and porcine somatotropin species containing an N-terminal phenylalanine as shown in FIGS. 3, 4 and 8. Thereafter, the bGH(A,L), bGH(A,V) and pGH(A) coding sequences were inserted into expression vectors such that the final gene sequence comprised, sequentially, a promoter, a ribosome binding site, an ATG start/methionine codon immediately adjacent the DNA coding sequence for either bGH(A,L), bGH(A,V) or pGH(A), and a translation stop codon. E. coli were then transfected with a given expression vector carrying the desired gene sequence and cultured under conditions which would allow for expression of the desired heterologous DNA and production of the desired heterologous protein. The proteins so produced were then sequenced and assayed for their appropriate biologic activity.

Thus, it has been discovered here that when a DNA sequence containing a start signal/methionine codon followed immediately by the codons for a heterologous N-alanyl polypeptide is expressed, the protein recovered from the procaryotic organism actually has alanine at the N-terminus, not a methionine. It is believed that a similar result is obtainable when that alanine codon is immediately preceded by up to about three contiguous methionine codons which include the start signal for translation of the mRNA encoding the desired polypeptide product. For example, the DNA including that translation start signal and the codons for the desired polypeptide product can include any sequence appropriately coding for met ala, met met ala, met met met ala, or any functional equivalent thereof.

An N-alanyl polypeptide is herein defined as a polypeptide having an alanine at its amino terminus. While applicant does not wish to be bound by the following theory of mechanism, it is believed that subsequent to translation, the N-terminal methionine of the polypeptide is enzymatically removed by the procaryote if the next amino acid is alanine or another amino acid having similar characteristics (e.g. polarity or hydrophobicity) that facilitate such removal of the N-methionine. It is furthermore believed that many procaryotes are capable of removing N-terminal methionines from heterologous and/or endogenous polypeptides when said N-terminal methionines are immediately followed by an alanine.

These procaryotes (e.g. various bacteria known and publicly available through recognized microorganism depositor institutions such as the ATCC or otherwise) include but are believed not limited to *E. coli* and various strains thereof. Indeed, it is contemplated that any procaryote capable of producing a polypeptide having an N-terminal alanine from a DNA coding sequence which begins with from one to about three contiguous methionine codons immediately followed by an alanine codon is potentially useful in the practice of the invention disclosed herein. Commercially and otherwise available procaryotic organisms may be screened for their ability to produce such N-alanyl polypeptides by inserting into the genome of said organisms a gene comprising sequentially a promoter operative in said organism, DNA encoding a ribosome binding site, from one to about three contiguous methionine codons including a translation start signal followed immediately by the codons for a heterologous N-alanyl polypeptide and a translation stop signal, thereafter causing expression of said gene and then determining the N-terminal amino acid sequence of the heterologous polypeptide so produced. When such a procaryotic organism has been found to produce internally such a heterologous N-alanyl polypeptide, that organism is within the class defined as "selected" for purposes of the disclosure and claims herein.

In a preferred embodiment of the present invention, three different isolates of *E. coli* strain K12 all of which have been deposited with the American Type Culture Collection, Rockville, Maryland, and have been assigned accession numbers ATCC 39936, 53010, and 53009 demonstrate an ability to remove N-terminal methionines when said N-terminal methionines are immediately followed by an alanine.

The present discovery is significant since it provides a method of producing in procaryotes heterologous polypeptides that have N-terminal alanines.

In one of the preferred embodiments, the method of the present invention is employed to generate two bGH species, bGH(A,L) and bGH(A,V), and one pGH species, pGH(A), free from other bovine or porcine proteins and/or other bGH or pGH species, respectively. Specifically, the method provides for production of bGH(A,L), bGH(A,V) or pGH(A) as single species. The ability to produce a single bGH or pGH species with amino acid sequences homologous to naturally occurring somatotropins has tremendous import for determining the precise bioreactivity of each bGH or pGH species given the numerous potentiating effects of bGH and pGH generally as cited above. In fact, it has been found that administering either of the two N-alanyl bGH species yields a potentiation of such bGH functions as milk production. Further, it has been found that administration of a lactation-enhancing amount of bGH(A,V) produced in accordance with the present invention increases milk production in dairy cows to a statistically (e.g. $p<0.05$) greater extent than similarly produced bGH(A,L). To date, there has been no teaching of the relative effectiveness of specific bGH forms (species) in enhancing milk production in lactating mammals. Furthermore, there has been no prior result, in vivo or in vitro, suggesting that a difference in bioactivity between bGH species would be observed. Thus, the finding that the valine allelic bGH species result in a greater enhancement in milk production than the leucine allelic bGH species was both surprising and unexpected. This finding further suggests that differences in the relative effectiveness of bGH species in potentiating such other growth hormone properties as increased feed efficiency and growth stimulation can similarly be defined. Thus, by employing the methods of the present invention which permit the production in bacteria of at least two of the molecular forms of pituitary bGH in essentially pure form and/or by employing other available technologies, the bGH species most effective in achieving a specific growth hormone induced response can now be produced. Such other available technologies include, but are not limited to, chemical synthesis of entire bGH proteins or fragments thereof, and/or production in other microorganisms such as yeast or in mammalian cells using known recombinant DNA techniques.

Additionally, once the bioactivity of each naturally-occurring species is determined, it is considered feasible to generate polypeptide variants of each of such species which would further increase their somatotropin activity. It is, therefore, anticipated that the generation of somatotropin variants by nucleotide or amino acid deletion, substitution and/or addition will provide various useful equivalents of the compositions disclosed herein. Such variants include an altered form of bGH(V) wherein the alteration comprises the addition of a methionine to the amino terminus. This variant, produced by genetically transformed bacteria, has also been found to increase lactation in dairy cows to a surprisingly great extent when administered in a lactation-enhancing amount. Furthermore, the extent of the observed increase in lactation pursuant to administration of this bGH(V) variant was found to be measurably greater than the lactation-enhancement observed pursuant to administration of an otherwise identical variant containing leucine at amino acid position 126.

While applicant does not wish to be bound by the following theory of mechanism, it appears that the substitution of valine for leucine at position 126 significantly enhances the bioavailability and/or bioreactivity of such somatrotropin protein(s). Specifically, x-ray crystallography performed on somatotropin proteins indicates that the region of said proteins from about amino acid 90 to about amino acid 135 constitutes a relatively flexible region. Studies of other proteins have shown that flexible regions often comprise a bioreactive site (e.g. a site which interacts with biologic receptors and/or other portions of the same protein to achieve a bioactive form). Thus, it is anticipated that additional variants of bGH (A,V), which variants comprise amino acid substitutions, deletions, additions and/or inversions within this described flexible region and/or outside this region that likewise result in a measurable enhancement of lactation (e.g. milk production) to a greater extent than otherwise-identical leucine bGH species or bGH (A,L), can be made. For example, changes at or around amino acid position 126 can include a substitution of other more hydrophilic and/or smaller amino acids (relative to leucine) providing that the described enhancement in milk production is not diminished to are intolerable degree.

Further, it is anticipated that valine bGH species containing an N-terminal phe$_1$, or an N-terminal ala$_{-1}$ can achieve the described enhancement in milk production when administered to cows. It is also anticipated that changes in the amino terminus (e.g. met$_{-1}$) which do not substantially differ from the N-terminus of naturally-occurring bGH would not interfere to an intolerable degree with the ability of valine bGH species to enhance milk production to a measurably greater extent than otherwise-identical leucine bGH species or bGH(A,L). It is further anticipated that a bGH composition wherein the concentration of valine bGH species, based on the weight of all bGH in the composition, is substantially greater than the concentration of valine bGH species in pooled pituitary bGH preparation would similarly achieve the described result.

In one of its broadest embodiments, the present invention is a refinement in the use of a recombinant DNA technology to directly produce in procaryotes heterologous polypeptides. Thus, the description of the invention presupposes knowledge of the basic techniques employed in recombinant DNA technology to isolate and clone DNA sequences encoding polypeptides, the rearrangement or altering of cloned DNA sequences, and the expression of cloned or modified DNA sequences in transformed microorganisms. Such techniques are within the skill of the art. (See, e.g., *Molecular-Cloning: A Laboratory Manual;* Maniatis, Fritsch & Sambrook eds. 1982).

ISOLATION AND/OR CONSTRUCTION OF HETEROLOGOUS DNA

In one embodiment of the present invention, the DNA sequence coding for the desired heterologous polypeptide to be produced in the procaryote is chosen and isolated, or a DNA sequence that encodes it is constructed or chemically synthesized. In many important embodiments, the polypeptide is a eucaryotic protein. If the polypeptide is small and the complete amino acid sequence known, a synthetic DNA molecule or sequence encoding the polypeptide can be constructed. If the amino acid sequence of the polypeptide is unknown, or its size is too large for the synthesis of a corresponding DNA sequence to be practical, a cDNA sequence can be prepared by reverse transcription from corresponding mRNA obtained from tissues or cells expressing the polypeptide. For example, in one embodiment of the present invention, the sequence for bGH can be so obtained from bovine pituitaries by now routine procedures described by Goodman et al. *Methods in Enzymology* 68:75-90 (1979). Alternatively, a cDNA sequence can be prepared from mRNA isolated from cells transformed with genomic DNA isolated from a native gene bank with an appropriate probe. Genomic DNA can also be modified in various vector systems such that the DNA can be expressed in procaryotes. These techniques are within the skill of the art.

Once a heterologous DNA sequence containing the codons for the desired polypeptide is obtained, it may be desirable to make certain modifications in the nucleotide sequence of the molecule. For example, if the molecule has been produced by reverse transcription from an mRNA template, it will often contain at least a portion of the DNA encoding the leader sequency of the preprotein. Thus, it is necessary to remove all of the leader-sequence DNA prior to the first codon of the desired protein. In some cases it may be necessary to add or substitute an alanine codon at the beginning of the sequence encoding the desired protein if it does not already have an N-terminal alanine codon. Then a translation start signal (which is also a methionine codon) is introduced upstream and immediately adjacent to the alanine codon. While the start signal/methionine codon will usually (and preferably) be the nucleotide sequence ATG, the sequence GTG can also occasionally serve as a start initiation signal/methionine codon. Additionally, the presence of more than one methionine codon, e.g. two, three or possibly more contiguous codons for methionine, is understood to constitute equivalence within the method of the present invention.

If not already present, at least one translation stop signal should be introduced after the codon for the C-terminal amino acid. Examples of translation stop signals include the deoxynucleotide triplets TAA, TGA, and TAG. In essence, therefore, recombinant DNA techniques are applied to construct a recombinant DNA sequence containing, sequentially, a translation start signal/methionine codon, the codons for the desired polypeptide with the N-terminal alanine codon adjacent to the start signal, and at least one translation stop signal adjacent to the codon for the C-terminal amino acid.

It has been found that efficient expression of mRNA can be hindered by secondary structures formed by the hydrogen bonding of two complementary series of nucleotides within the mRNA. Elimination of these complementary sequences, particularly in that portion of the molecule that encodes the N-terminus, facilitates the binding of ribosomes to the mRNA and therefore, increased levels of expression. It may be desirable, therefore, to replace codons that participate in the formation of such secondary structures with codons for the same amino acid, but comprised of a different nucleotide triplet. See European Patent 75,444 (published Mart. 30, 1983); Seeburg et al., (1983) DNA 2:37-45 and Shoner et al (1984) *Proc. Nat'l Acad. Sci. U.S.A.* 81:5403-5407.

Other approaches to constructing the heterologous DNA sequences will be apparent to those skilled in the art. For example, if a DNA molecule is available that encodes a polypeptide which is expressed with an N-terminal structure of NH2-met-x-y . . . where x is an amino acid other than alanine, an alanine codon can be inserted between the translation start signal/methionine codon and the codon for x. Alternately, the codon for x may be deleted and an alanine codon inserted in place thereof. Thus, a protein having the N-terminal structure NH2-ala-x-y . . . or NH2-ala-y . . . , respectively, would be produced in the process of the present invention.

Similarly, deletions, additions and/or substitutions in any of the amino acid codons within a given gene sequence may be made so that a variant polypeptide would be expressed in the process of the present invention. A "variant" polypeptide is defined herein as having single or multiple amino acid deletions, substitutions and/or additions as compared to the naturally occurring amino acid sequence of a given polypeptide. Examples of such variants include but are not limited to met-bGH(L) and met-bGH(V) wherein the amino acid sequence of these variant bGH species are identical to the bGH(L) and bGH(V), respectively, produced by bovine pituitary cells except for the presence of an additional methionine at the N-terminus. These variant polypeptides are constructed as having an amino acid sequence essentially the same as that of a naturally occurring polypeptide as long as the biologic activity is not diminished to an intolerable degree. Creation and expression of variant polypeptides may be desirable in order to achieve increased accumulation, increased protein stability, to facilitate polypeptide purification, and/or in optimizing biological activity.

The above modifications of the DNA molecule encoding the desired polypeptide can be accomplished using restriction enzymes, exonucleases, endonucleases, etc. by techniques known in the art. The general techniques of oligonucleotide-directed site-specific mutagenesis can also be employed to effect the above modifications in the structure or sequence of the DNA molecule and are known to those of skill in the art. See e.g., Zoller & Smith (1982) *Nuc. Acids Res.* 10:6487-6500; Zoller & Smith, (1983) (*Meth. Enzymol.* 100:468:500; Norris et al., (1983) (*nuc. Acids Res.* 11:5103-5112.

In accordance with recombinant DNA techniques, once the desired heterologous DNA sequence is obtained, the sequence is then inserted into an appropriate cloning vector which provides a means for replicating the DNA sequence. Any appropriate cloning vector, preferably containing a marker function, may be used, for example *E. coli* plasmid vectors which include Col EI, Hershfield et al., *Proc. Nat'l. Acad. Sci. U.S.A.* (9174) 71:3455; pBR322, Boliver et al., *Gene* (1977) 2:95; pBR325, Soveron et al., *Gene* (1978) 4:121; and pkc7, Rao et al., *Gene* (1979) 7:79; and *E. coli* bacteriophage vectors which include Charon λL47.1, Loenen et al., *Gene* (1980) 10:249; M13m;8 and M13mp9, Messing et al., *Gene* (1982) 19:269. The general techniques for inserting said DNA sequence into a cloning vector to create a recombinant vector are within the skill of the art. See e.g., *Molecular Cloning: A Laboratory Manual;* Maniatis, Fritsch & Sambrook, eds. (1982).

Once multiple copies of the desired heterologous DNA sequence are obtained, these sequences may be removed from the recombinant vectors and inserted into an expression system for production and isolation of the desired heterologous protein as described more fully below. Modifications of the heterologous DNA sequence, by methods known to those skilled in the art may be made prior to insertion of these DNA sequences into an expression vector or following said insertion.

Figure 1:
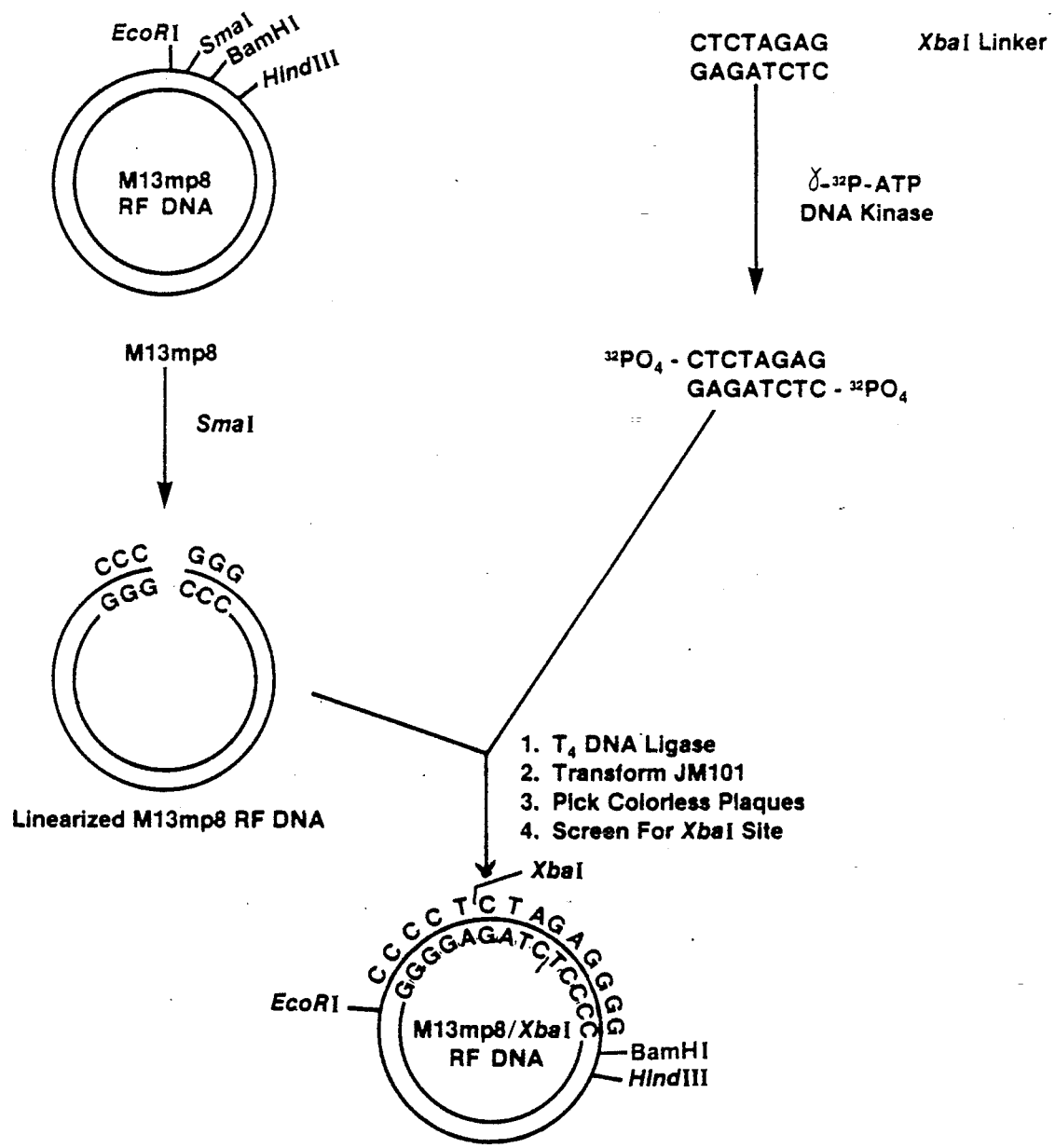
FIG. 1 depicts the construction of M13mp8/XbaI comprising a M13mp8 vector having inserted therein at the SmaI restriction endonuclease site an XbaI restriction endonuclease site.
Figure 5:
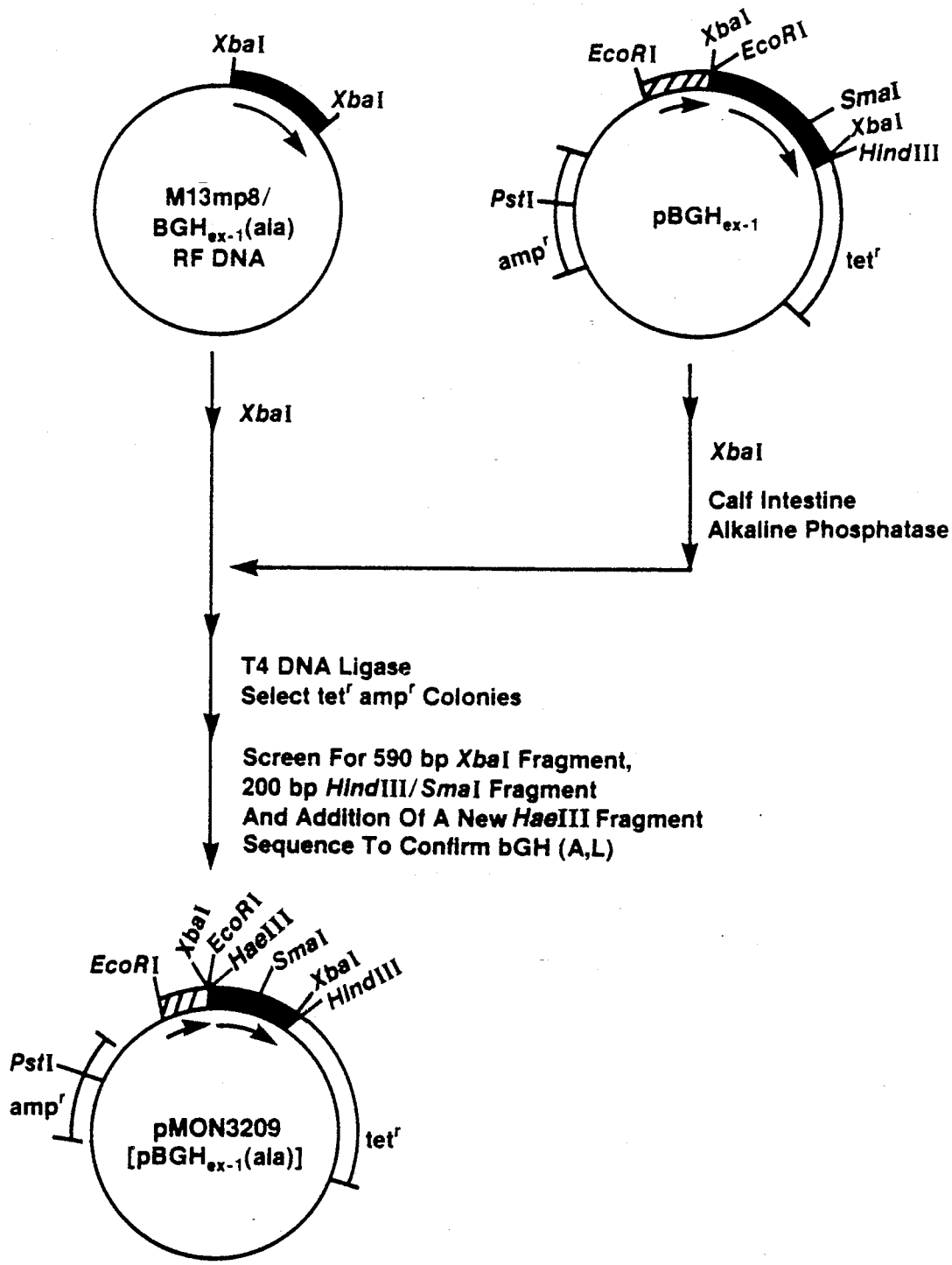
FIG. 5 depicts the construction of a pMON3209 expression vector comprising pBGH$_{ex-1}$ carrying a bGH(A,L) DNA coding sequence in place of a bGH(L) DNA coding sequence.
Figure 6:
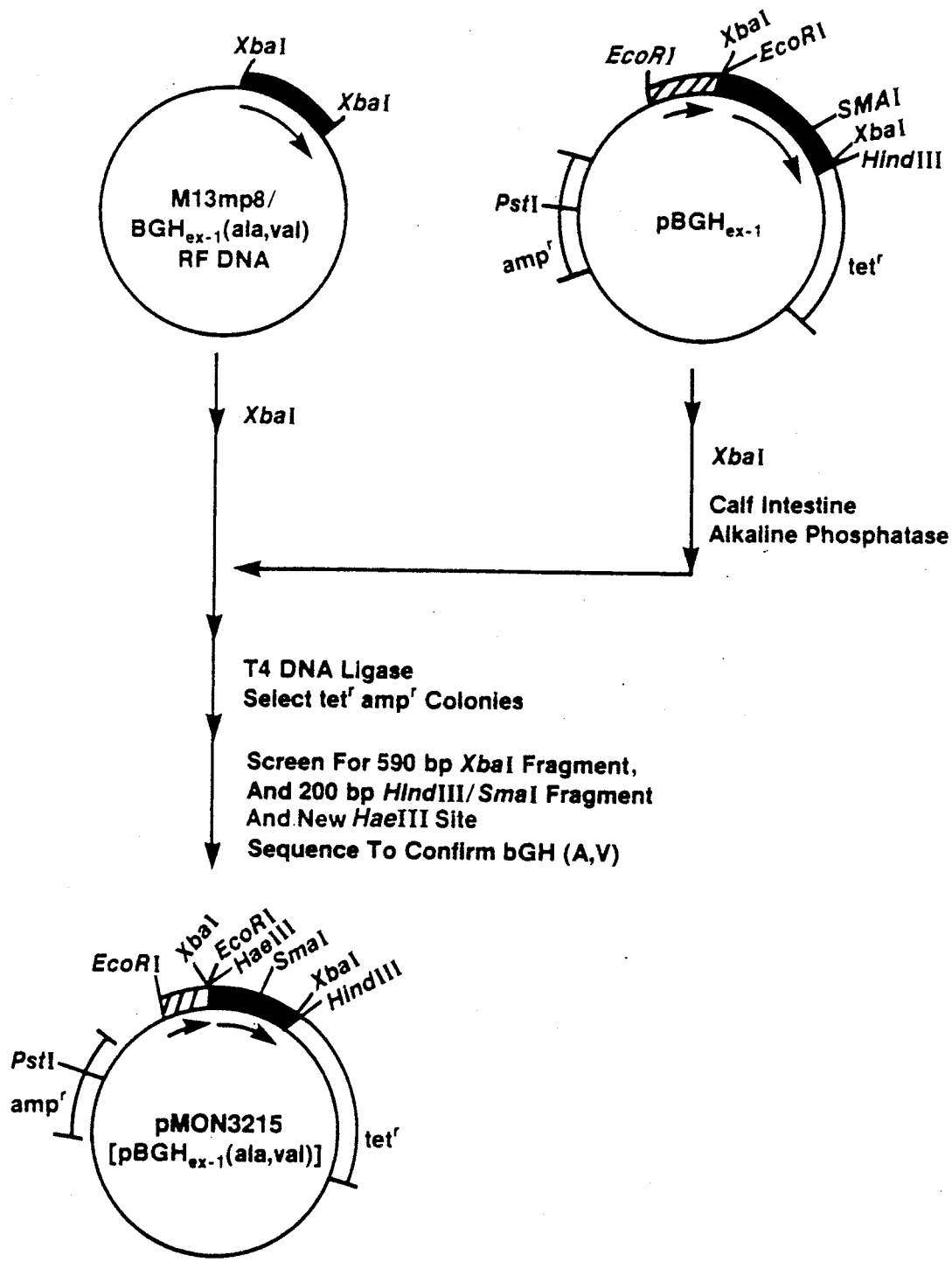
FIG. 6 depicts the construction of a pMON3215 expression vector comprising pBGH$_{ex-1}$ carrying a bGH(A,V) DNA coding sequence in place of a bGH(L) DNA coding sequence.
Figure 10:
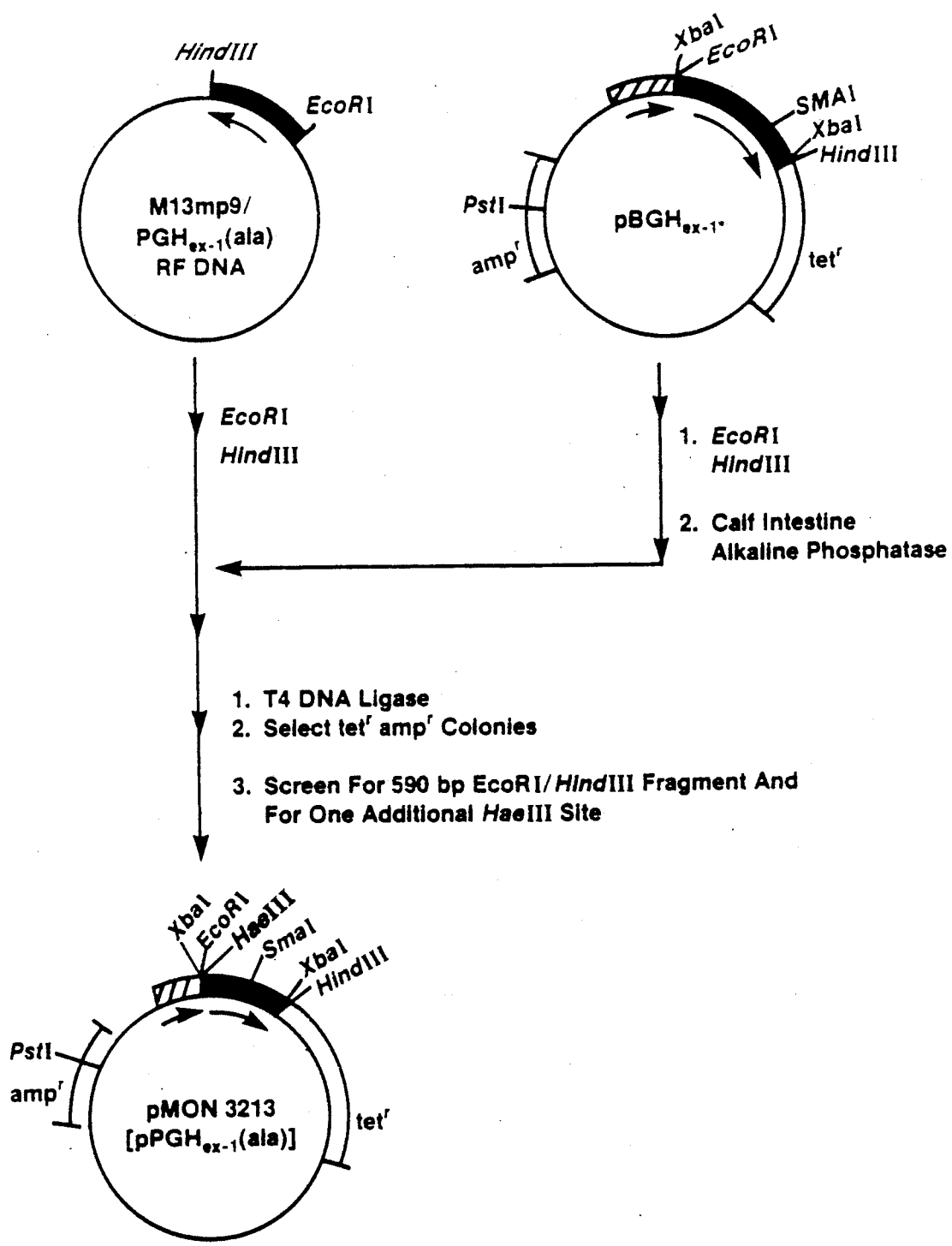
FIG. 10 depicts the construction of a pMON3213 expression vector comprising pBGH$_{ex-1}$* carrying a pPGH(A) DNA coding sequence in place of a bGH(L) DNA coding sequence.

In the examples of the present invention, M13mp8, described by Messing et al., *Gene* (1982) 19:269, modified to contain an XbaI restriction site as shown in FIG. 1, was chosen as a cloning vector along with M13mp9, ID. The M13mp8 and M13mp9 vectors, collectively "M13 vectors", allow for isolation of recombinant vectors in both double-stranded (ds) or replicative form (RF) and single-stranded (ss)DNA forms. Isolation of RF DNA recombinant vectors facilitates the subsequent insertion of the replicated desired DNA sequences into expression vectors, as shown in FIGS. 5, 6, and 10. Alternatively, isolation of the single-stranded form of these recombinant vectors facilitates both isolation of recombinant vectors which contain the desired DNA sequence in a proper 5' to 3' orientation for expression and the creation of any DNA sequence modification by such techniques as oligonucleotide-directed site-specific mutagenesis, as shown in FIGS. 3, 4 and 8. Additionally, these M13 vectors can accommodate DNA fragments or genes up to 4kb in length which insures the cloning of a typical, entire, eucaryotic gene sequence.

Figure 2:
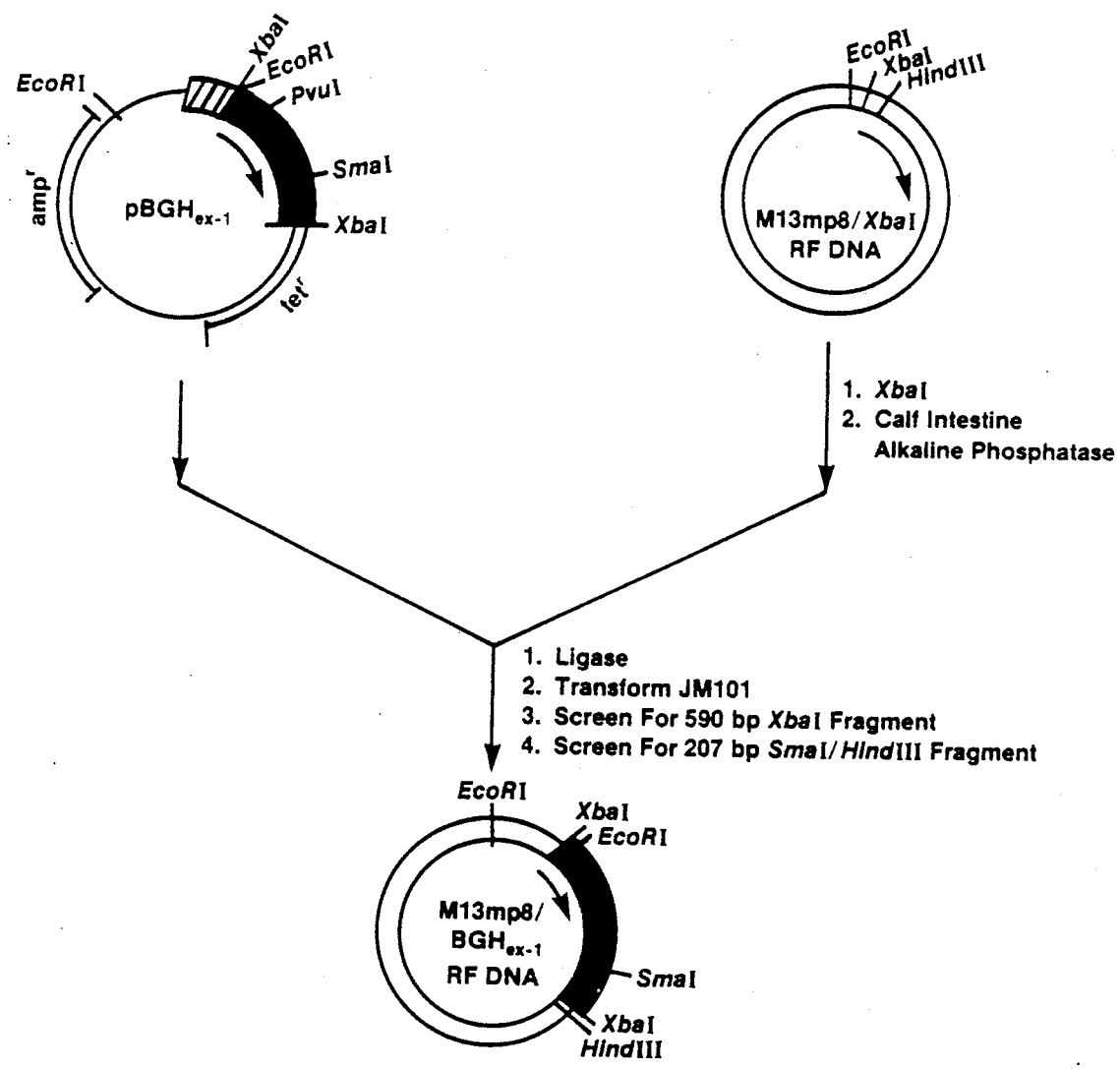
FIG. 2 depicts the construction of M13mp8/BGM$_{ex-1}$ comprising M13mp8/XbaI carrying a bGH(L) DNA coding sequence.

The marker function employed in the M13 vectors, as described by Messing et al., *Gene* (1982) 19:269, involves the enzyme for β-galactosidase. Specifically, the desired heterologous DNA sequence is inserted into the lacZ gene fragment carried on the M13 vector which disrupts the normal complementation of the lacZ gene fragment carried on the M13 vector with the partial lacZ gene fragment carried on the chromosomal DNA of the host cell (e.g. *E. coli* JM101) so that said host is no longer capable of metabolizing lactose present in the bacterial growth medium. *E. coli* infected with M13 vectors which do not have a foreign gene sequence inserted into the vector borne lacZ gene fragment are capable of metabolizing lactose present in the bacterial growth medium and yield characteristic blue plaques when the bacteria are grown on agar containing 1×YT medium comprising 0.8% (w/v) tryptone, 0.5% (w/v) yeast extract, 0.5% (w/v) NaCl and a color indicator for β-galactosidase. The plaque coloration of *E. coli* infected with recombinant vectors carrying an inserted heterologous DNA sequence in the M13 lacZ gene fragment is clear or colorless when the bacteria are grown on said medium. Hence, positive insertion of the heterologous DNA sequence into these cloning vectors is identified by colorless plaque formation following infection of the *E. coli* host cell with the recombinant vector. Insertion of the DNA sequences encoding bGH(L) and pGH(P) into M13 vectors are shown in FIGS. 2 and 9, respectively.

Figure 7:
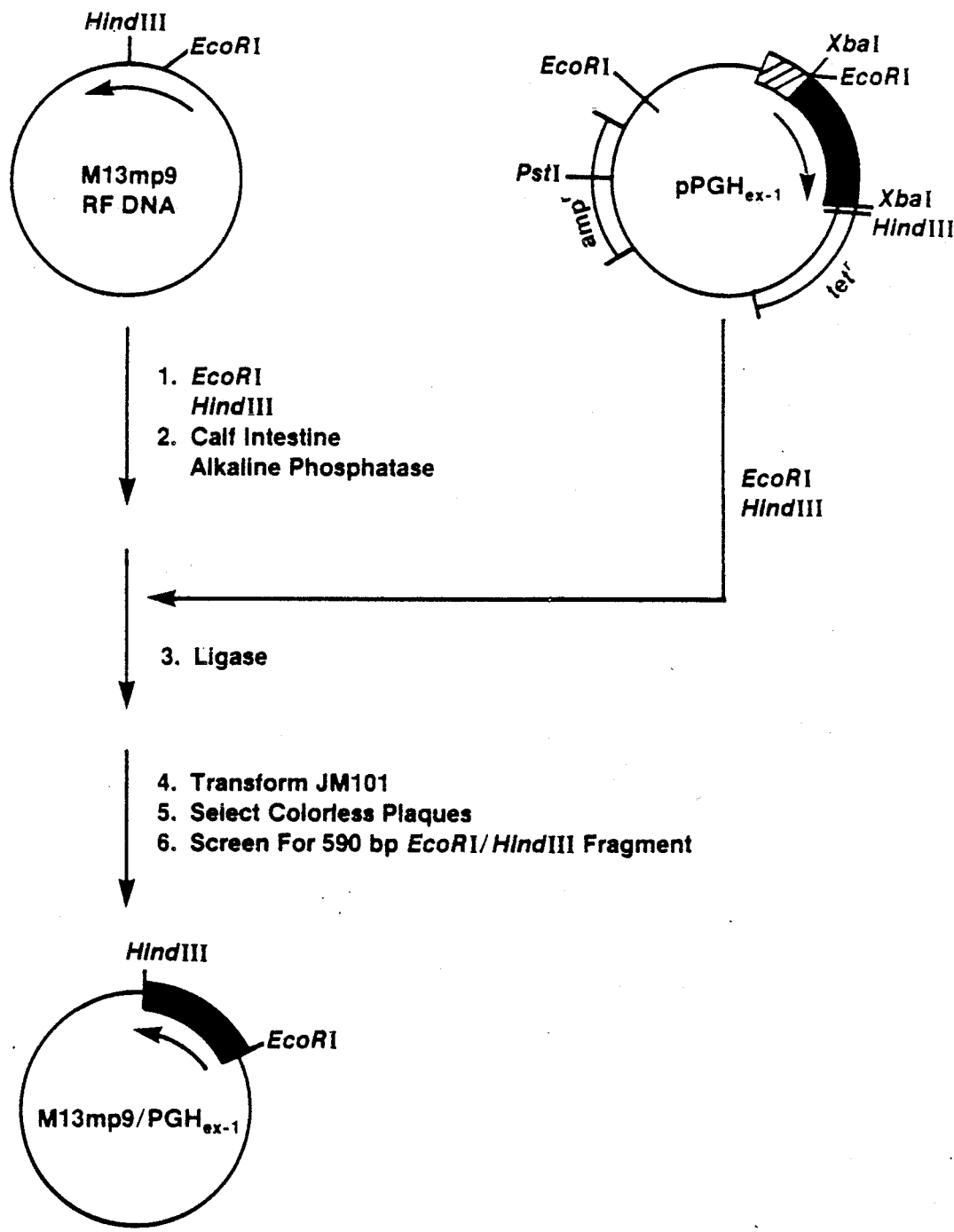
FIG. 7 depicts the construction of M13mpg/PGH$_{ex-1}$ comprising M13mpg carrying a pGH(P) DNA coding sequence.

In a preferred embodiment, bGH(L) and pGH(P) DNA coding sequences carried on bacterial plasmids pBGH$_{ex-1}$ and pPGH$_{ex-1}$, respectively, as in Seeburg et al., *DNA* (1983) 2(1):37-45, were isolated from these plasmids by site-specific restriction endonuclease cleavage. It should be noted that bacteria transfected with bacterial plasmids pBGH$_{ex-1}$ or pPGH$_{ex-1}$, respectively, and subsequently cultured under conditions which permit expression of the bGH(L) and pGH(P) coding sequences, respectively, produce somatropins with an N-terminal methionine (e.g. met-bGH(L) or met-PGH(P), respectively). The respective sequences were then inserted into RF DNA of a modified M13mp8 vector (M13mp8/XbaI) and M13mp9 vector as shown in FIGS. 2 and 7, respectively. Insertion of the desired bGH(L) and pGH(P) DNA sequences into M13mp8/XbaI and M13mp9 RF DNA was confirmed by site-specific restriction endonuclease cleavage as again shown in FIGS. 2 and 7, respectively. *E. coli* MJ101 were then transfected with one of these recombinant vectors as described by Messing et al., *Methods in Enzymology* (1983) 101:20 and the ssDNA of the recombinant vectors isolated as described by Messing et al., *Gene* (1982) 19:269. Relevant portions of these references by Messing et al. are incorporated herein by reference.

Once isolated, the ssDNA's of these recombinant vectors were modified by oligonucleotide-directed site-specific mutagenesis to create the DNA coding sequences for bGH(A,V), bGH(A,L), bGH(V) and pGH(A). Specifically, bGH(L) was modified to add a codon for alanine, e.g. GCC, at the 5'-end of the bGH(L) coding sequence as shown in FIG. 3. It is anticipated that any of the four codons for alanine may be so added. The preferred alanine codon for optimal somatotropin yield in the expression system employed herein is GCC. Confirmation of the addition of an alanine codon to create a bGH(A,L) coding sequence was achieved by DNA sequence analysis of the entire or 5'-end of the bGH(A,L) DNA sequence by the method of Sanger et al., *Proc. Nat'l. Acad. Sci., U.S.A.* (1977) 74:5463.

The bGH(A,V) coding sequence was created by aligonucleotide-directed site-specific mutagenesis of the bGH(A,L) coding sequence as shown in FIG. 4, by converting the leucine codon at amino acid position 127 [in bGH(A,L)] to a valine codon, e.g. GTG. It is again anticipated that any codon for valine may be employed in this conversion. The creation of a bGH(A,V) coding sequence was again confirmed by DNA sequence analysis of the resultant bGH(A,V) coding sequence.

The bGH(V) coding sequence which results in production of met-bGH(V) proteins in bacteria transfected with an expression vector comprising the bGH(V) coding sequence was similarly created by oligonucleotide-directed site-specific mutagenesis of the bGH(L) coding sequence by converting the leucine codon at amino acid position 126 [in bGH(L)] to a valine codon, e.g. GTG.

The creation of a pGH(A) coding sequence by oligonucleotide-directed site-specific mutagenesis of the pGH(P) coding sequence was similarly performed as shown in FIG. 8 and described more fully below, and confirmed by DNA sequence analysis.

Having now isolated and constructed the desired heterologous DNA sequences, as exemplified for bGH(A,L), bGH(A,V) and pGH(A), these sequences may be replicated and numerous copy numbers generated by propagation of the respective recombinant vectors by methods known to those skilled in the art and referenced above. These heterologous DNA sequences may now be inserted into any appropriate expression vector for production in procaryotes of the desired heterologous polypeptides.

PRODUCTION OF N-TERMINAL ALANINE POLYPEPTIDES

As discussed previously, an appropriate expression vector should contain the necessary transcription and translation signals for production of a heterologous protein in the chosen host cell along with a marker function for identification of those expression vectors into which the desired heterologous DNA sequence has been inserted. By use of a procaryotic expression vector, the recombinant DNA sequences can be added to the genetic complement of a procaryotic organism via transduction, transformation or transfection (collectively referred to herein as "transfection") and said organism can then be cultured under conditions (generally governed by the promoter and host employed) that cause the desired polypeptide to be produced. Thus the "genomic" DNA of the organisms used in this invention contain both chromosomal and episomal DNA.

A number of expression vectors have been described for heterologous gene expression and heterologous protein production in procaryotic host cells and are known to those skilled in the art.

In one preferred embodiment of the present invention, expression vectors pBGH$_{ex-1}$, see Seeburg et al., DNA (1983) 2(1):37-45, and pBGH$_{ex-1}$*, comprising a modified pBGH$_{ex-1}$ vector, were employed.

The bGH$_{ex-1}$ expression vector is a pBR322 bacterial plasmid carrying a gene for bGH(L). The gene comprises, in sequence, a tryptophan promoter Pptrp), a Shine-Delgarno sequence, an ATG translation start-/methionine codon immediately adjacent the N-terminal phenylalanine coding sequence, the first amino acid of the bGH(L) polypeptide, the bGH(L) coding sequence and a translation stop codon. The marker function on the pBGH$_{ex-1}$ expression vector is antibiotic resistance. Specifically, pBGH$_{ex-1}$ carries two antibiotic resistance genes, one for ampicillin (amp$^r$) and the second for tetracycline resistance (tet$^r$) which confer specific antibiotic resistance to otherwise susceptible host cells stably transformed with the expression vector. Thus, stable transformants may be selected for by growth in media containing either tetracycline, ampicillin or both antibiotics.

In the examples of the present invention, expression vectors pMON3209 and pMON3215 comprising pBGH$_{ex-1}$ carrying bGH(A,L) and bGH(A,V) coding sequences, respectively, in place of the bGH(L) coding sequence were generated as shown in FIGS. 5 and 6, respectively. A bacteria such as E. coli, was then stably transformed with one of these expression vectors and transformants selected by growth on media containing the appropriate antibiotic. The expression plasmids contained within the transformed bacteria were then screened for the presence of the bGH(A,L) and bGH(A,V) coding sequences in the correct 5' to 3' orientation by restriction enzyme cleavage.

In an example of the present invention, pBGH$_{ex-1}$* comprising the pBGH$_{ex-1}$ vector modified by the removal of the EcoRI restriction site located upstream from the 5'-end of the ptrp coding sequence, was employed to create the expression vector pMON3213 carrying the pGH(A) coding sequence in place of the bGH(L) coding sequence. The resultant pBGH$_{ex-1}$* vector contains only a single EcoRI site as shown in FIG. 9. The replacement of the pGH(A) coding sequences for the bGH(L) coding sequence in pBGH$_{ex-1}$* to create the expression vector pMON3213 is shown in FIG. 10. E. coli were then transformed with said mixture and transformants selected by growth in antibiotic-containing media. The expression plasmids contained within the transformed bacteria were then screened for the presence of the pGH(A) coding sequences by restriction cleavage.

Production of bGH(A,L), bGH(A,V) or pGH(A) in E. coli was achieved by transforming either E. coli W3110, E. coli LE392 or E. coli strain 294, deposited and having ATCC accession numbers 39936, 3010, and 53009, respectively, with one of the expression vectors, pMON3209, pMON3215 or pMON3213 in accordance with the method described more fully below. The transformed E. coli W3110 were then cultured under conditions which permit expression of the somatotropin genes and production of the desired heterologous polypeptides.

Purification of the heterologous peptide produced will depend on both the protein and host cell chosen. It has been observed, for example, that the heterologous proteins produced in such bacteria as E. coli are often precipitated within the cell in the form of "refractile" bodies. The term "refractile" is used because these bodies can actually be seen using a phase contrast microscope. A method useful in recovering heterologous proteins, in biologically active form is described in European Patent Application 114,506 (published Aug. 1, 1984) incorporated herein by reference. Briefly, this purification method comprises concentrating the host cells, lysing these cells to generate a cellular extract or homogenate and then isolating the refractile bodies by differential centrifugation, all the steps of which are known to those skilled in the art. The isolated refractile bodies are dissolved in a strong denaturant such as guanidine hydrochloride and the solubilized protein is then exchanged in a suitable solvent for example, urea, purified by chromatographic means, and finally biologically activated, i.e., permitted to assume its active configuration and then oxidized so that such configuration is maintained by disulfide bonds between its appropriate cysteine residues, as described in European Application 114,506. A more detailed purification of such heterologous proteins is described in two con currently filed U.S. applications, one by S. B. Storrs entitled "Method of Somatotropin Solubilization" and the second by L. A. Bentle, S. B. Storrs and J. W. Mitchell entitled "Method of Somatotropin Naturation", incorporated herein by reference. These two concurrently filed U.S. patent applications and the present application are all commonly assigned to Monsanto Company. Subsequent purification of the heterologous polypeptide to rid it of contaminating bacterial proteins can be achieved by conventional chromatographic means such as gel filtration or ion exchange chromatography. Typically, the resulting purified compositions will contain, by weight, from about 90% to about 99.5% of the N-alanyl polypeptide and from about 0.5% to about 10% protein native to the bacteria or other procaryotic host in which the polypeptide was produced.

It has been found that usually at least about 80% of the heterologous peptide expressed by the method of this invention has an N-terminal structure of $NH_2$-ala . . . . The remaining polypeptide is typically in the methionyl form, having an N-terminal structure of $NH_2$-met-ala . . . . By varying growth conditions and/or timing of the induction of gene expression, however, it is possible to raise the proportion of polypeptide with alanine at the N-terminal to at least about 95% or even greater.

In a particularly preferred embodiment of the present invention, the somatotropin polypeptide species produced and isolated as described above were shown to exhibit somatotropin-like biological activity as assayed in the rabbit liver receptor assay performed as described by Tsushima and Friesen, *J. Clin. Endocrinol. Metab.* (1973) 37:334–337 and a rat weight gain bioassay. In the latter assay, the bioactivities of the *E. coli* produced somatotropins are assessed relative to a known lot of somatotropin (e.g. bovine or porcine pituitary somatotropin) by relating the amount of weight gain of hypophysectomized rats to varying amounts of injected compound. Specifically, titrated dosages (between 0 and 60 micrograms) of the unknown or standard somatotropin source are injected into hypophysectomized rats (95–135 g) on a daily basis for 7 or more days. Using multiple regression, body weight gains of animals receiving the known and unknown hormone lots are regressed on log transformed dosages. The slopes are tested to insure nonparallelism and intercept commonality. Bioactivities are reported as the ratio of the slopes times the activity of the standard.

Use of the N-alanine bGH products of this invention increases milk production by cows and are believed to decrease the amount of feed required for a given output of milk by such cows. Administration to dairy cows of a lactation-enhancing amount of bGH species containing a valine at or around position 126 of the mature bGH protein is particularly well suited for potentiating milk production by these cows. Such products of this invention may be administered to cows by injection, infusion or implantation in polymers or other media known to achieve the delivery of a required dosage in the circulatory system. Pharmaceutically acceptable base formulations such as solutions, emulsions or gels may be used, either encapsulated or not. These formulations may contain a single bGH species or variant thereof or any prescribed combination of naturally-occurring and/or variant polypeptides [e.g. a mixture of bGH(A,V) and bGH(A,L) and/or a mixture of bGH(A,V) and met-bGH(A)]. Dosages may range from at least about 0.005 mg to about 200 mg per animal per day and preferably from about 5 mg to about 40 mg per animal per day. The amount most effective for increasing milk production and/or feed-to-milk efficiency may be determined by routine experimentation. The actual preferred dosage of bGH is dependent on such variables as the size, general health and nutritional status of the specific animal. Although milk production can be used to assess the effect of bGH on cows, other production properties of the cows, such as overall growth rate and meat production can also be employed. bGH can, if desired, be administered to cows with other beneficial agents such as other biologically active proteins, antigens, or the like, and thereby provide enhanced effects.

As previously discussed, the invention also contemplates the production of variants of bGH which have an N-terminal alanine but which have deletions, additions, inversions and/or substitutions along the polypeptide chain. Such modifications having desirable lactation and/or growth enhancing properties can be identified by routine testing in cows.

The following examples illustrate preferred embodiments of the present invention and are not intended to limit the invention's scope in any way. While this invention has been described in relation to its preferred embodiments, various modifications thereof will be apparent to one skilled in the art from reading this application.

MICROORGANISMS AND PLASMIDS

The following microorganisms are available from the American Type Culture Collection (ATCC), 12301 Parklawn Drive, Rockville, Md., 20852, U.S.A.:

ATCC 39936—*E. coli* W3110
ATCC 53010—*E. coli* LE392
ATCC 53009—*E. coli* strain 294
ATCC 53024—*E. coli* W3110 (pMON3209)
ATCC 53022—*E. coli* W3110 (pMON3215)
ATCC 53023—*E. coli* W3110 (pMON3213)

These deposits are available to the public upon the grant of a U.S. patent to the assignee of this application, Monsanto Company. These deposits will be available for the life of any such U.S. patent having the benefit of the filing date of this application. However, it should be understood that the availability of a deposit does not constitute a license to practice the subject invention in derogation of patent rights granted by governmental action. Furthermore, the present invention is not to be limited in scope by the microorganisms deposited, since the deposited embodiments are intended only as specific illustrations of the invention.

EXAMPLE 1

All oligonucleotides were synthesized in the Department of Biological Sciences, Monsanto, employing an Applied Biosystems DNA synthesizer in accordance with the procedure set forth by the manufacturer, Applied Biosystems, Inc., Foster City, Calif. Restriction enzymes and DNA modifying enzymes were purchased from New England Biolabs (Beverly, Mass., New England Nuclear (Boston, Mass.) and Bethesda Research Laboratories (BRL) (Gaithersburg, Md.). An XbaI linker was obtained from Collaborative Research, Inc. (Lexington, Mass.). T4 DNA ligase was purchased from BRL (Gaithersburg, Md.). T4 DNA kinase was purchased from New England Biolabs (Beverly, Mass.). $^{32}P$-labeled nucleotides were purchased from Amersham (Arlington Heights, Ill.) E. coli DNA polymerase I, Klenow fragment, was purchased from New England Nuclear (Boston, Mass.). E. coli JM101 was obtained from Dr. Jo Messing, University of Minnesota (St. Paul, Minn.).

Restriction enzyme digestions, the T4 DNA ligase reactions, and E. coli DNA polymerase I, Klenow fragment, reactions may be carried out in accordance with the procedures set forth by the manufacturers. Preferred buffers for the following restriction enzymes are as follows: for XbaI: 100mM NaCl, 50mM tris, pH 7.5, 10mM MgSO$_4$; for EcoRI, Hind III and Sma I: 50mM NaCl, 10mM Tris, pH 7.5, 10mM MgSO$_4$. T4 DNA ligase reactions were run in buffers containing 25mM Tris, pH 8.0, 10mM MgCl$_2$, 10mM dithiothritol (DTT), 2mM spermidine and 0.2mM ATP. E. coli DNA polymerase I, Klenow fragment, was used in a buffer containing 20mM Tris, pH 7.2, 10mM MgCl$_2$, 10mM (DTT), 1mM ATP, and 1mM each dATP, dGTP, dCTP, dTTP. Alpha-$^{32}$P-dATP (400 ci/mmol) was added to the Klenow reaction if labeling of the newly synthesized DNA strand was desired.

Oligonucleotides were labeled using gamma-$^{32}$P-ATP (sp. act. greater than 5000 ci/mmol) and T4 DNA kinase in 100mM Tris, pH 8.0, 10mM MgCl$_2$, 5mM DTT.

Plasmids carrying DNA coding sequences for bGH(L) and pGH(P) (pBGH$_{ex-1}$ and pPGH$_{ex-1}$, respectively) were obtained from Genentech, Inc., So. San Francisco, Calif. These plasmids can be prepared as described in European Patent Application 75,444 (published Mar. 30, 1983 ; Seeburg et al., DNA (1983) 2(1):37–45; Goeddel et al. Nature (1979) 281:544–548; DeBoer et al., in Promoters: Structure and Function (1982); M. J. Chamberlin and R. Rodriguez eds., Chapter 293; Miozzari and Yanofsky, J. Bacteriol. (1978) 133: 1457–1466; and Rosenberg and Court, Annual Review of Genetics 13:319–353. As shown in European Application 75,444 (DeBoer et al), the first 21 translated codons in the DNA for bGH(L) are ATG TTC CCA GCT ATG TCT CTA TCT GGT CTA TTC GCT AAC GCT GTT CTT CGT GCT CAG CAT CTT or functional equivalents thereof. (Functional equivalents of those codons can of course be used alternatively.) Other relevant portions of these publications are incorporated herein by reference.

M13mp8 and M13mp9 were obtained from Dr. Jo Messing, University of Minnesota (St. Paul, Minn.).

All bacterial growth media components and antibiotics were obtained from either Sigma (St. Louis, Mo.) or Difco Laboratories (Detroit, Mich.).

EXAMPLE 2

The following example demonstrates the construction of three DNA coding sequences which, when expressed, provide for the direct production in bacteria of polypeptides containing an N-terminal alanine. Specifically, DNA coding sequences were constructed such that the translation initiation start/methionine codon (ATG) is immediately followed by an alanine codon (e.g. GCC). The three DNA coding sequences, comprising bGH(A,L), bGH(A,V) and pGH(A), were constructed by oligonucleotide-directed site-specific mutagenesis of previously isolated somatotropin DNA sequences. This example also demonstrates the construction of a bGH(V) DNA coding sequence which when expressed in bacteria causes production of met-bGH(V).

a. Construction of a bGH(A,L) DNA Coding Sequence

The somatotropin, bGH(L), DNA coding sequence was excised from pGH$_{ex-1}$ as an XbaI fragment and cloned into the XbaI site of a modified M13mp8 vector (M13mp8/XbaI). Construction of the M13mp8/XbaI vector which contains an XbaI linker in the original SmaI site is shown in FIG. 1. As shown in FIG. 2, XbaI cleaves at either end of the bGH(L) DNA coding sequence thus excising the complete bGH(L) coding sequence. The XbaI restricted pBGH$_{ex-1}$ plasmid was mixed in the presence of T4DNA ligase with RF M13mp8/XbaI DNA linearized by XbaI restriction enzyme cleavage and treated with calf intestine alkaline phosphatase. The mixture was then incubated overnight at 14° C. Treatment with calf intestine alkaline phosphatase prevents recircularization of the M13mp8/XbaI vector. Insertion of the bGH(L) DNA coding sequence into the M13mp8/XbaI vector to create recombinant vector M13mp8/BGH$_{ex-1}$ was initially ascertained by colorless plaque formation on a lawn of bacteria, E. coli JM101, grown on 1×YT medium employing the soft agar overlay procedure described in Molecular Cloning: A Laboratory Manual, Maniatis, Fritsch & Sambrook, eds. (1982) pg. 64, which included 10 μl 100mM IPTG (isopropyl-β-D-thiogalactopyranoside) and 50 μl 2% (w/v) X-GAL(5-bromo-4chloro-3-indolyl-β-D- galactopyranoside) in 3 ml of top agar, and transfected with said recombinant vector as previously described. Insertion of the bGH(L) coding sequence was confirmed by cleavage of isolated RF DNA, Molecular Cloning: A Laboratory Manual, Maniatis, Fritsch & Sambrook, eds. (1982), Chapter 3, of the recombinant vector with XbaI which yields a 590 base pair fragment comprising the inserted sequence. The 590 base pair fragment was identified by agarose gel electrophoresis in one percent (w/v) agarose as described in Molecular Cloning: A Laboratory Manual, Maniatis, Fritsch & Sambrook, eds. (1982). All subsequent restriction fragments were identified by this referenced method. The orientation of the inserted bGH(L) coding sequences was ascertained by cleavage of the RF recombinant vector with SmaI and HindIII. When the coding sequences are in the correct 5' to 3' orientation, cleavage with these restriction enzymes should yield a 207 base pair fragment. The isolation of ss phage DNA was conducted in accordance with the method of Messing et al., Gene (1982) 19:269. The M13mp8/BGH$_{ex-1}$ vector was then employed as a template in the oligonucleotide-directed site-specific mutagenesis essentially as described by Zoller and Smith, Nuc. Acids Res. (1982) 10:6487–6500, Zoller and Smith Methods in Enzymol. (1983) 100: 46–500. Norris et al., Nuc. Acid Res. (1983) 11:5103–5112, the relevant portions of which are herein incorporated by reference.

FIG. 3 diagrams the mutagenesis procedure for creation of a DNA coding sequence for bGH(A,L) from the bGH(L coding sequence. Briefly, an oligonucleotide primer (see Table 1, below) containing the sequence of the desired mutation is used to prime synthesis of a closed-circular DNA copy of the ssDNA M13mp8/BGH$_{ex-1}$ template. The closed-circular dsDNA molecules thus generated are separated from incomplete and ssDNA circles by alkaline sucrose gradient centrifugation as described by Zoller and Smith, Methods in Enzymol. (1983) 100:468–500. The closed-circular dsDNA molecules are then used to transform E. coli JM101 as described by Messing et al., Gene (1982) 19:269–276 and the resulting colorless plaques are lifted onto Pall filters obtained from Pall Ultrafine Filtration Corp. (Glen Cove, N.Y.) and screened for hybridization to a $^{32}$P-labeled form of the oligonucleotide primer used to generate the site-specific mutagenesis. The lifting of said plaques was conducted in accordance with methods described by the Pall Filter manufacturer. Hybridization screening was carried out using nylon Biodyne filters as described by Pall Ultrafine Filtration Corporation (Glenn Cove, N.Y.) in their "Protocol Guide for DNA Transfer to Pall Biodyne ™ A Nylon Filters" (1983). Filters were washed at increasing temperatures until the radiolabeled signal was removed from a control filter which was prepared with M13mp8/bGH$_{ex-1}$ phage. A typical filter washing protocol employed a room temperature wash in 6×SSC 0.9M NaCl and 0.09M NaCitrate) for ten minutes followed by a 50° C. wash in 6×SSC for five minutes and subsequent washings at temperatures increasing by 5° C. Plaques which hybridized to radiolabeled oligonucleotide primer at temperatures higher than the control phages were presumed to carry the newly created bGH(A,L) coding sequence and were termed potential positives. Alternatively, individual colorless plaques were picked from the *E. coli* JM101 transformations and grown in 5 milliliters (ml) of 2×YT medium (1.6% (w/v) tryptone, 1.0% (w/v) yeast extract, 0.5% (w/v) NaCl) overnight at 37° C. with aeration. Phage DNA, prepared in accordance with Messing et al., *Gene* (1982) 19:269, was then spotted onto nitrocellulose, hybridized with radiolabeled primer, and washed in increasing temperatures as described above. Phage DNA which showed hybridization temperatures higher than M13mp8/bGH$_{ex-1}$ control plaques were similarly termed potential positives. Potential positive plaques from both screening procedures were grown as described above and used to prepare ss phage DNA, which was then sequenced according to the procedure of Sanger et al. *Proc. Nat'l Acad. Sci., U.S.A* (1977) 74:5463 to confirm that they carried the bGH(A,L) coding sequence. The RF DNA of M13mp8/BGH$_{ex-1}$ (ala) was also screened by restriction enzyme analysis with Hae III to confirm the addition of an alanine codon following the start signal/methionine codon ATG as the alanine codon creates an additional Hae III restriction site. The frequency of addition of the alanine codon was about 2% to the bGH(L) DNA coding sequence.

b. Construction of a bGH(A,V)DNA Coding Sequence

Construction of the bGH(A,V) DNA coding sequence, screening and sequence confirmation were carried out using the same procedure as above except that the template was M13mp8/BGH$_{ex-1}$ (ala), as shown in FIG. 4, and the oligonucleotide primer was as shown in Table 1, below. The frequency of conversion of the leucine codon to a valine codon was about 10%.

c. Construction of a bGH(V) DNA Coding Sequence

Construction of the bGH(V) DNA coding sequence, screening and sequence confirmation were carried out using the same procedure as above. Specifically, the template was M13mp8/BGH$_{ex-1}$ and the oligonucleotide primer was the same as employed to create bGH(A,V. The frequency of conversion of the leucine codon to a valine codon was, again, about 10%.

d. Construction of a pGH(A,) DNA Coding Sequence

Oligonucleotide-site-specific mutagenesis was similarly employed to add an alanine codon to the pGH(P)DNA coding sequence described by Seeburg et al., *DNA* (1983) 2(1):37–45. The mutagenesis procedure as diagramed in FIG. 8 was conducted as follows.

The 590 base pair pGH(P) DNA coding sequence carried on the pPGH$_{ex-1}$ plasmid was removed from the plasmid by restriction enzyme cleavage with EcoRI and HindIII which cleave the plasmid at the 5'-and 3'-ends of the pGH(P) coding sequence, respectively, as shown in FIG. 7. The restricted pPGH$_{ex-1}$ plasmid was then mixed with M13mp9 RF DNA similarly cleaved with EcoRI and HindIII but additionally pretreated with calf intestine alkaline phosphatase to prevent religation of the M13mp9 restriction fragments. T4 DNA ligase was then added to said mixture. Owing to the abberrant ends on both the RF phage DNA and pGH(P) DNA coding sequence created by the use of two different restriction enzymes, the pGH(P) DNA will selectively be inserted into the RF phage DNA and will be inserted in the correct 5' to 3' orientation as shown in FIG. 7. *E. coli* JM101 were then transformed, as described above for M13mp8/BGH$_{ex-1}$, with the recombinant M13mp9/PGH$_{ex-1}$ vector carrying the pGH(P) DNA coding sequence The transformed *E. coli* JM101 were then grown on 1×YT medium containing colorimetric reagents and selected by colorless plaque formation as described previously. Insertion of the pGH(P) DNA coding sequences was confirmed as follows. Colorless plaques were picked and RF M13mp9/PGH$_{ex-1}$ DNA, isolated as previously described, was then cleaved with EcoRI and Hind III and subjected to agarose gel electrophoresis yielding a 590 base pair fragment comprising the inserted pGH(P) DNA. M13mp9/PGH$_{ex-1}$ phage were then propagated in *E. coli* JM101 and the ss phage DNA isolated as described above.

The M13mp9/PGH$_{ex-1}$ DNA was then employed as a template for the oligonucleotide-site-specific mutagenesis, shown in FIG. 8, in accordance with the procedure described above for creation of a bGH(A,L) coding sequence, employing a specific primer (see Table 1, below). The frequency of addition of an alanine codon, herein GCC, to the pGH(P) coding sequence was approximately 12%. The resultant pGH(A) coding sequence was again confirmed by DNA sequence analysis.

TABLE 1

Creation of N-terminal Alanine Somatotropin Coding Sequences

| Protein Designation | Primer Sequence[1] | Template | Plasmid Designation[2] |
|---|---|---|---|
| met-bGH(V) | 5'GGTGCCATCTTCCACCTCCCGCATCAG | M13mp8/BGH$_{ex-1}$ | pMON3214 |
| bGH(A,L) | 5'GACATAGCTGGGAAGGCCATAGAATTCTAG | M13mp8/BGH$_{ex-1}$ | pMON3209 |
| bGH(A,V) | 5'GGTGCCATCTTCCACCTCCCGCATCAG | M13mp8/BGH$_{ex-1}$(ala) | pMON3215 |

TABLE 1-continued

Creation of N-terminal Alanine Somatotropin Coding Sequences

| Protein Designation | Primer Sequence[1] | Template | Plasmid Designation[2] |
|---|---|---|---|
| pGH(A) | 5'CCAGTGAATTCTATGGCCTTCCCAGCTATG | M13mp9/PGH$_{ex-1}$ | pMONN3213 |

[1]The underlined bases in the primer sequence code for the desired addition or mutation.
[2]The designations refer to the final plasmids which are used for the direct production of the N-terminal alanine containing polypeptides in E. coli

EXAMPLE 3

This example demonstrates the construction and expression of three recombinant expression vectors which provide for the direct production in bacteria of polypeptides containing an N-terminal alanine. The three polypeptides so produced are the somatotropin species bGH(A,L), bGH(A,V) and pGH(A). This example also demonstrates the construction and expression of bGH(V) and expression of bGH(L). The polypeptides so produced are met-bGH(V) and met-bGH(L), respectively.

a. Expression of bGH(A,L) bGH(A,V), bGH(L) and bGH(V)

The bGH(A,L), bGH(A,V) and bGH(V) DNA coding sequences carried on recombinant vectors M13mp8/BGH$_{ex-1}$(ala), M13mp8/BGH$_{ex-1}$ (ala,val), and M13mp8/BGH$_{ex-1}$(val), respectively, were used to replace the bGH(L) DNA coding sequence carried on the pBGH$_{ex-1}$ expression plasmid (see FIGS. 5 and 6). This was done by digestion of the respective M13 RF DNA's with XbaI. Expression plasmid pBGH$_{ex-1}$ was also digested with XbaI and subsequently treated with calf intestine alkaline phosphatase to prevent religation of the restriction framents. Each of the digested RF DNA's were then separately mixed with the digested and treated pBGH$_{ex-1}$ DNA and ligated as described previously overnight at 14° C. The recombinant expression vectors thus formed were labeled pMON3209, pMON3215 and -pMON3214 carrying the bGH(A,L), bGH(A,V), and bGH(V) DNA coding sequences, respectively. E. coli W3110 were then transformed with the ligation mixture containing pMON3209 or pMON3215 or pMON3214 or pBGH$_{ex-1}$ and grown in Lauria Broth (LB) comprising 1% (w/v) tryptone, 0.5% (w/v) yeast extract and 0.5% (w/v) NaCl and containing 12.5 μg/ml tetracycline and 200 μg/ml ampicillin. E. coli W3110 containing pMON3209 have ATCC accession number 53024. E. coli W3110 containing pMON3215 have ATCC accession number 53022. Transformation was conducted, briefly, as follows. Approximately 50 ml of E. coli W3110 were grown in LB media to an OD600=0.60. The cells were then pelleted and resuspended in 10 ml Buffer A comprising 25mM Tris, pH 7.6, and 10mM NaCl. The cells were then pelleted and resuspended in 1 ml Buffer A to which 14 ml Buffer B comprising 25mM Tris, pH, 7.6, 10mM NaCl, 50mM CaCl$_2$, was added and the suspension incubated on ice for 30 minutes. The cells were then pelleted and resuspended in 3 ml Buffer B. An aliquot of 0.2 ml of resuspended cells was then mixed with 0.1 ml Buffer B and 0.1 to 5.0 μg of the desired recombinant expression vector (pMON3209 or pMON3215 or pMON3214 or BGH$_{ex-1}$) and incubated on ice for 60 minutes. The incubated mixture was then heated for one minute at 37° C. after which time 3 ml LB media was added and the resustant mixture then incubated 60 minutes at 37° C. The cells were then pelleted and resuspended in 300 ml LB media and grown on LB plates containing antibiotics as previously described. Resistant colonies were then selected and the pMON3209, pMON3215, pBGH$_{ex-1}$ and pMON3214 expression vector DNA's isolated in accordance with the procedure described in Molecular Clonings: A Laboratory Manual, Maniatis, Fritsch & Sambrook, eds. (1982). The pMON3209, pMON3215, pBGH$_{ex-1}$ and pMON3214 DNA's were screened for the presence of a 590 base pair XbaI fragment and a 200 base pair HIND III/SmaI fragment showing the presence of the bGH(A,L), bGH(V) and bGH(A,V) DNA coding sequences in the correct orientation. The pMON3209 and pMON3215 expression plasmids were further screened by restriction analysis with HaeIII to confirm the presence of a new HaeIII site resulting from the addition of a GCC(alanine) codon. Finally, the 590 base pair XbaI fragment from the pMON3209, pMON3214 and pMON3215 vectors were partially sequenced as described previously to confirm the presence of the bGH(A,L), bGH(V) and bGH(A,V) DNA coding sequences in these expression vectors.

Single colonies of E. coli W3110 carrying pMON3209, pMON3214, BGH$_{ex-1}$, or pMON3215 were inoculated separately into 5 ml of LB containing 12.5 ug/ml tetracycline and grown overnight at 37° C. with aeration. 0.5 ml of the overnight cultures were then used to separately inoculate 25 ml of M9 media comprising (per liter of media) 100 ml 10×salts (70 grams (g) Na$_2$HPO$_4$, 30g KH$_2$PO$_4$, 5g NaCl, 10g NH$_4$Cl per 1000 ml total volume) 1.2 ml 1M MgSO$_4$, 0.25 ml 0.1% B$_1$, 12.5 ml 20% (w/v) glucose, ).025 ml 1M CaCl$_2$, supplemented with 0.5% (w/v) casamino acids and 6.25 ug/ml tetracycline, contained within 250 ml flasks. The inoculants were then each grown at 37° C. with aeration until reaching an OD600 (optical density at 600 nanometers)=1.0. An aliquot of 0.2 ml was next removed from each of said flasks and individually lysed in sodium dodecyl sulfate (SDS)-polyacrylamide gel electrophoresis (PAGE) buffer and assayed by SDS-PAGE in accordance with Laemmli, Nature (1970) 227:680-685. Proteins of 22,000 daltons were at high levels in E. coli W3110 from both of the two gene constructs. Furthermore, both 22,000 dalton proteins bound in Western blot assays (see Krivi and Rowold, Hybridoma (1984) 3:252-262) to a monoclonal antibody, F11-A1-B6, (see Id.) produced against bovine pituitary somatotropin, thereby confirming that the polypeptides are related to pituitary somatotropin. E. coli W3110 cells carrying the parental pBR322 plasmid do not produce a protein of 22,000 daltons that binds to antisomatotropin antibodies.

Bacteria carrying the expression plasmids pMON3209, pMON3214, pBGH$_{ex-1}$ and pMON3215 were stored as follows. A single colony of E. coli W3110, transformed with one of the plasmids (pMON3209 or pMON3215 or pMON3214 or pBGH$_{ex-1}$), was grown overnight at 37° C. in 5ml LB plus 12.5 ug/ml tetracycline with aeration. A 1 ml aliquot from each overnight culture was added separately to individual flasks containing 25 ml LB plus 12.5 ug/ml tetracycline and grown to an OD600=1.0. The cells from each flask were then harvested by centrifugation at 6000×g at 4° C. for 5 minutes. The pellets were individually resuspended in 12 ml LB plus 7.5% (v/v) DMSO and immediately frozen on dry ice in 1 ml aliquots. The cells were then stored in a liquid nitrogen freezer. Additionally, about 10 micrograms of purified plasmid DNA was stored at −80° C.

b. Expression of pGH(A) DNA Coding Sequence

As shown in FIG. 10, the pGH(A) coding sequence carried on the recombinant vector M13mp9/PGH$_{ex}$-$_1$(ala) was used to replace the bGH(L) DNA coding sequence carried on a modified pBGH$_{ex-1}$ expression vector. The modified expression vector, pBGH$_{ex-1}$*, comprises a pBGH$_{ex-1}$ expression vector wherein the EcoRI restriction site located upstream from the tryptophan promoter (ptrp) has been removed (see FIG. 9). The modified pBGH$_{ex-1}$* expression vector was created by partial EcoRI digestion of pBGH$_{ex-1}$* followed by SI nuclease treatment to remove the sticky ends. The restricted pBGH$_{ex-1}$ vector was then recircularized by use of T4 DNA ligase and used to transform E. coli JM101, all as previously described. Plasmid DNA from single colonies was next screened for a 590 base pair EcoRI/HindIII fragment carrying the pGH(A) coding sequence and a 1050 base pair EcoRI/PstI fragment carrying the ptrp sequence (See FIG. 9). Removal of this EcoRI restriction site facilitates the site specific insertion of the pGH(A) coding sequence into the pBGH$_{ex-1}$* expression vector in the proper orientation as shown in FIG. 10. The recombinant expression vector thus formed is hereinafter referred to as pMON3213. The mixture containing pMON3213 was then used to transform E. coli W3110 and the transformants grown and selected for as described above. E. coli W$_{3110}$ containing pMON3213 have ATCC accession number 53023. Replacement of the pBGH(L) coding sequence with a pGH(A) coding sequence in the pBGH$_{ex-1}$* expression vector was confirmed by isolating pMON3213 DNA and then cleaving said expression vector with EcoRI and Hind III to generate a 590 base pair fragment and cleavage with Hae III to show the presence of an additional Hae III restriction fragment generated by the presence of an alanine codon in the pGH(A) CNA coding sequence. Final confirmation of the presence of the pGH(A) DNA coding sequence in the pMON3213 expression vector was made by partially sequencing the EcoRI/Hind III 590 base pair fragment as previously described.

Expression of the pGH(A) DNA coding sequence and production of pGH(A) in E. coli W3110 was achieved in the manner set forth for bGH(A,L) and bGH(A,V) production described above. Similarly, high levels of a protein of 22,000 daltons, demonstrable by SDS/PAGE as described above, were achieved.

E. coli W3110 carrying the pMON3213 expression vector were stored as previously described and employed in large scale (10 to 100 liter fermentation) production of pGH(A) also as previously described. The pGH(A) protein content in the 100-liter batch fermentation was, again, approximately 1 g/liter of broth by radioimmunoassay of Rosner et al., J. Immunol. Methods (1982) 52:175-181.

EXAMPLE 4

This example was performed in order to determine the N-terminal amino acid sequence of the heterologous proteins, bGH(A,L), bGH(A,V), met-bGH(V), met-bGH(L) and pGH(A), produced in bacteria as examples of the method of the present invention.

The somatotropin polypeptides produced in E. coli were purified from crude solubilized refractile bodies containing either bGH(A,L), bGH(A,V), met-bH(V), met-bGH(L) or pGH(A) by immunoadsorbent chromatography as described by Krivi & Rowold, Hybridoma (1984) 3:151-161. All three somatotropin species purified by immunoadsorbent chromatography appeared to be greater than 95% pure by SDS-PAGE analysis of 1 ug purified protein run on a 7.5 to 15% (w/v) gradient gel performed in accordance with the method of Laemmli, Nature (1970) 227:680-685. Proteins concentrations of the purified bGH species were determined by routine high performance liquid chromatography analysis.

Proteins purified by immunoaffinity chromatography for use in N-terminal sequence analysis were dialyzed exhaustively against water and then lyophilized. Prior to N-terminal sequence analysis, the purified proteins were resuspended in ammonium bicarbonate buffer comprising 50mM ammonium bicarbonate plus 0.1% (w/v) SDS and dialyzed against the same buffer to remove residual tris(hydroxymethyl) amino methane(tris) and glycine. An Applied Biosystems Protein Sequencer Model 470A (Applied Biosystems, Inc. Foster City, Calif.) was then employed for all N-terminal sequencing analysis, as described by Hankapiller et al. (1983), Methods in Enzymol. 91:399-413 and Hunkapiller et al. (1983), Methods in Enzymol. 91:486-493.

Table 2, below, shows the results of the sequence analysis for several preparations of bGH(A,L), bGH(A,V), met-bGH(V), met-bGH(L) and pGH(A) polypeptides. The amount of protein with N-terminal methionine is shown in the table as a percentage of the total somatotropin in the sample. Two methods were used for methionine quantification. With the indirect method the amount of NH2-met-ala-phe . . . in a predominantly NH2-ala-phe . . . population was calculated from differences in lag signals. Since this procedure depends on an estimate of "normal" sequence lag, which varies form cycle to cycle, it is only a crude estimate of the NH2-ala-phe . . . sequence present. The direct method comprising an Edman degradation reaction compared signal strength of PTH-met to PTH-ala after separation of PTH-met from chemical noise by high performance liquid chromatography (HPLC). "PTH" refers to phenyl-thiohydantion. Specifically, the Edman degradation sequencing reaction consists of reacting the N-terminal amino acid with a reagent that causes cleavage of that amino acid and its subsequent release as a PTH-derivative of that amino acid. The latter procedure will give good estimates of % met-ala-phe . . . as long as free amino acid contamination is low.

As shown by the N-terminal sequencing results presented in Table 2, below, no evidence for methionine processing is seen when the N-terminal methionine is followed by phenylalanine. However, 80% or more of the molecules produced from the MBS(A,L) and MBS(A,V) gene constructs have alanine rather than methionine at the N-terminal. The extent of N-terminal methionine processing is variable in cells from different fermentation runs, but always occurs in at least 80% of the somatotropin molecules. Additionally, production levels of approximately 10 to 15% of the total bacterial protein were achieved for the somatotropins produced in the transformed microorganisms.

tained using bGH(A,L), and about 17% greater form met-bGH(V) as compared to met-bGH(L). Such unexpected productivity advantages provided by the valine bGH species of this invention are clearly of very great potential economic benefit to dairymen.

TABLE 2

TABLE 3

Milk Production Response Associated with Injection of Solubilized bGH Species In Cows

| Treatment | N[b] | Weeks of Study[a] | | | | Change Relative to Control | % Change Relative to Control | Probability of Significance |
|---|---|---|---|---|---|---|---|---|
| | | 1 | 2 | 3 | 1–3 | | | |
| control | 10 | 25.5 | 24.6 | 26.0 | 25.4 | — | — | |
| bGH(A,V) | 9 | 32.2 | 33.1 | 36.7 | 34.0 | 8.6 | 33.9 | |
| bGH(A,L) | 9 | 29.9 | 30.2 | 33.5 | 31.2 | 5.8 | 22.8 | |
| met-bGH(V) | 8 | 31.6 | 33.8 | 35.8 | 33.7 | 8.3 | 32.7 | |
| met-bGH(L) | 9 | 31.0 | 32.1 | 34.2 | 32.5 | 7.1 | 28.0 | |
| bGH(A,V) vs bGH(A,L) | | | | | | | | $p = 0.02$ |
| met-bGH(V) vs met-bGH(L) | | | | | | | | $p = 0.33$ |
| Val vs Leu | | | | | | | | $p = 0.02$ |

[a]Values are based on least-squares means of kilograms per cow per day adjusted for pretreatment 3.5 percent fat-corrected milk.
[b]"N" refers to the number of cows employed in each treatment.

N-Terminal sequence analysis of met-bGH(L), bGH(A,L), bGH(A,V) and pGH(A) proteins.

| Sample | % N-Terminal Methionine[1] | |
|---|---|---|
| | Indirect | Direct |
| met-bGH(L) | 92.0 | 100.0 |
| bGH(A,L) | 20.3[2] | 18.4[2] |
| | 10.8 | <6.0 |
| bGH(A,V) | 7.5[2] | <3.0[2] |
| | 16.7 | 9.0 |
| pGH(A) | 16.7 | 17.0 |
| met-bGH(V) | not done | 100.0 |

[1]The amount of protein with N-terminal methionine is shown as a % of the total somatotropin in a sample.
[2]The two numbers represent the data for protein purified from 2 independent fermentations.

EXAMPLE 5

This example was performed in order to determine the ability of the bGH species produced in bacteria to stimulate milk production in dairy cows. As shown in Table 3 below, both bGH (A,V) and met-GH(V) unexpectedly stimulated milk production to a greater extend than their respective leucine containing analogues, bGH(A,L) and met-bGH(L). Additionally, the valine bGH species tested when compared collectively against the leucine bGH species tested showed a statistically (p=0.02) greater enhancement of milk production.

The study was conducted briefly as follows. Holstein cows in their second and third trimester of lactation were given 5 milliliters (ml) sodium bicarbonate solution, pH 9.8±0.5, alone (herein referred to as "control sample") or containing about 25 milligrams (mg) of bGH(A,V), bGH(A,L), met-bGH(V) or met-bGH(L) (herein collectively referred to as "test somatotropins"), daily. All test somatotropins and control samples were administered parenterally by intramuscular injection into the semitendinosus muscle daily for 21 consecutive days. The individual milk production of each cow was recorded at each PM and AM milking beginning six days prior to the first daily injection through day 21 of injection. Milk fat, protein and somatic cells were analyzed weekly by the DHIA Test Laboratory at DHIA Testing Center, Springfield, Miss., 65803. The results presented in Table 3, below indicate that the increase in milk production resulting from administration of bGH (A,V) to cows was about 50% greater than that ob-

I claim:

1. A method for enhancing lactation of a cow comprising administering to said cow a lactation enhancing amount of a composition comprising bovine growth hormone (bGH) including bGH(V) having a valine at the position of leucine/valine heterogeneity corresponding to amino acid 126 in pituitary bGH wherein the concentration of said bGH(V) based on the total weight of bGH in said composition is greater than about 30 percent.

2. A method of claim 1 wherein the concentration of said bGH(V) is greater than 50%.

3. A method of claim 1 wherein said bGH(V) has an alanine at the amino terminus thereof.

4. A method of claim 1 wherein said bGH(V) has a methionine at the amino terminus thereof.

5. A method of claim 3 wherein said bGH(V) has an amino acid sequence essentially the same as naturally occurring pituitary bGH.

6. A method of claim 4 wherein said bGH(V) has an amino acid sequence essentially the same as naturally occurring pituitary bGH.

7. A method of claim 1 wherein said composition is essentially free from naturally occurring protein of bovine origin.

8. A method for enhancing lactation of a cow comprising administering to said cow a lactation enhancing amount of essentially pure bGH(V) having a valine at the position of leucine/valine heterogeneity corresponding to amino acid 126 in pituitary bGH.

9. A method of claim 8 wherein said bGH(V) has an alanine at the amino terminus thereof.

10. A method of claim 8 wherein said bGH(V) has a methionine at the amino terminus thereof.

11. A method of claim 9 where said bGH(V) has an amino acid sequence essentially the same as a naturally occurring pituitary bGH.

12. A method of claim 10 wherein said bGH(V) has an amino acid sequence essentially the same as a naturally occurring pituitary bGH.

13. A method of claim 8 wherein said bGH(V) is produced by recombinant DNA techniques and is essentially free from naturally occurring proteins of bovine origin.

* * * * *